US007666997B2

(12) United States Patent
Kaelin et al.

(10) Patent No.: US 7,666,997 B2
(45) Date of Patent: *Feb. 23, 2010

(54) METHODS OF TREATMENT USING NBS-1, ANTIBODIES AND PROTEINS THERETO, AND USES OF THE ANTIBODIES

(75) Inventors: William Kaelin, Boston, MA (US); Christine Jost, Jamaica Plain, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 156 days.

This patent is subject to a terminal disclaimer.

(21) Appl. No.: 10/155,059

(22) Filed: May 24, 2002

(65) Prior Publication Data

US 2002/0147173 A1  Oct. 10, 2002

Related U.S. Application Data

(62) Division of application No. 09/081,975, filed on May 12, 1998, now Pat. No. 6,451,979.

(60) Provisional application No. 60/046,207, filed on May 12, 1997.

(51) Int. Cl.
*C07K 16/00* (2006.01)

(52) U.S. Cl. .................. 530/387.1; 530/350; 530/388.1; 530/391.3

(58) Field of Classification Search .............. 530/387.1, 530/350, 388.1, 391.3
See application file for complete search history.

(56) References Cited

U.S. PATENT DOCUMENTS

| 4,478,744 | A | * | 10/1984 | Mezei et al. | |
| 5,001,225 | A | | 3/1991 | Taylor | |
| 5,468,468 | A | * | 11/1995 | LaRochelle et al. | |
| 2004/0253232 | A1 | * | 12/2004 | Jakobovits et al. | 424/141.1 |
| 2005/0202016 | A1 | * | 9/2005 | Caput et al. | 424/146.1 |

FOREIGN PATENT DOCUMENTS

WO  WO 97/28186  8/1997

OTHER PUBLICATIONS

Roitt et al (Immunology, 1993, Mosby, St. Louis, p. 6.4-6.5).*
Herbert et al (The Dictionary of Immunology, Academic Press, 3rd Edition, London, 1985, pp. 58-59.*
Vojtesek et al (Br. J. Cancer, 1993, 67:1254-8.*
Roitt et al, 1998, Immunology, 4th ed, Mosby, London, (p. 7.7-7.8).*
Holmes (Exp. Opin.Invest. Drugs, 2001, 10(3):511-519).*
Herbert et al. (The Dictionary of Immunology, Academic Press, 4th edition, 1995, p. 58).*
Greenspan et al. (Nature Biotechnology 7:936-937 (1999)).*
See http://www.answers.com/topic/antigenic-determinant-1, Antigenic Determinant.*
Cruse et al (Illustrated Dictionary of Immunology, CRC Press, New York, p. 241, 1995).*
Stratagene Catalog 1988, p. 39.*
Genbank A35658.*
Genbank I40377.*
Genbank T13230.*
Geysen et al (1984, PNAS, 81:3998).*
Agarwal et al (1996, J. Immunol., 157:2779-2787).*
Stites and Terr Eds, Basic and Clinical Immunology, Seventh Edition,, 1991, Appleton and Lange, East Norwalk, Connecticut.*
Xu et al (Onc., 27:3501-3507, 2008).*
Greenspan et al. (Nature Biotechnology. 1999; 7: 936-937).*
Daniel et al (Virology, 202:540-549, 1994).*
Immunology for Life Scientists (Ed. Eales, p. 14, 2003).*
Bost et al. (Immunol. Invest. 1998; 17:577-586).*
Weiss et al (PNAS, 88:5484-5488, 1991).*
Ben-Yehoyoda et al (JBC, 273(36):34475-34482, 2003).*
M. Kaghad et al., "Cell", 90(4):808-819 (1997).
S. Dickman, "Science", 277(5332):1605-1606 (1997).
C. Jost et al., "Nature", 389(6647):191-194 (1997).
B. Clurman et al., "Nature", 389(6647):122-123 (1997).
M. Oren, "Cell", 90(5):829-832 (1997).
Levine, et al., "Nature", 351:453-456 (1991).
Hollstein et al., "Science", 253:49-53 (1991).
Haffer et al., "Curr Opin. Genet. Dev.", 5:84-90 (1995).
Kern et al., "Science", 256:827-830 (1992).
Versteeg et al., "Eur. J. Cancer", 31A:538-541 (1995).
Bowie et al., "Science", 247:1306-1310 (1990).
Burgess et al., "J. Cell. Bio.", 111:2129-2138 (1990).
Lazar et al., "Molecular and Cellular Biology", 8:1247-1252 (1988).
Herbert, "The Dictionary of Immunology, Academic Press, Loneon", p. 58 (1996).
Shuster et al., "Cell Motility Cytoskeleton", 35:175-187 (1996).
Webster's II New Riverside Dictionary, The Riverside Publishing Co., Boston, p. 1262 (1988).
Kaghad et al., (Y11416), Genbank Sequence Database (Acession E308621), National Center for Biotechnology Information, National Library of Medicine, Bethesda, Md) (1998).
Yang et al., (AFO75436), Genbank Sequence Database (Acession G3695094), National Center for Biotechnology Information, National Library of Medicine, Bethesda, MD) (1998).
Osada et al., (AB16073), Genbank Sequence Database (Acession D1033557), National Center for Biotechnology Information, National Library of Medicine, Bethesda, MD) (1988).
Vojtesek et al., (Oncogene, 10:389-393) (1995).
Queen et al., (PNAS, 86:10029-10033) (1989).

* cited by examiner

*Primary Examiner*—Stephen L Rawlings
*Assistant Examiner*—Brad Duffy
(74) *Attorney, Agent, or Firm*—Fish & Richardson P.C.

(57) ABSTRACT

Antibodies that will specifically bind to NBS-1 are described. It is also shown that NBS-1 will interact with p53 responsive elements in a p53 promoter. Thus, NBS-1 can be used in subjects having a p53-dependent tumor to inhibit growth of that tumor.

8 Claims, 20 Drawing Sheets

Human p73α/Human p53

```
p73α  MAQS..TATSPD GGTTFEHLWS SLEPDSTYFD LPQSSRGNNE VVGGTDSSMD
p53   MEEPQSDPSVEPPL SQETFSDLWK LLPE.......... NNV LSPLPSQAMD

51
      VFHLEGMTTS VMAQFNLLSS TMDQMSSRAA SASEYTPEHAASVPTHSPYA
      DLML   SPD DIEQWFTEDP GPDEAPRMPE AAPPVAPAPAAPTPA APAP
      42

101
      QPSSTFDTMS PAPVIPSNTD YPGPHHFEVT FQQSSTAKSA TWTYSPLLNK
      APSWPL.... .SSSVPSQKT YQGSYGFRLG FLHSGTAKSV TCTYSPALNK
      88

151
      LYCQLAKTCP IQLKVSTPPP PGTAIRAMPV YKKAEHVTDV VKRCPNHELG
      MFCQLAKTCP VQLWVDSTPP PGTRVRAMAI YKQSQHMTEV VRRCPHHE
      133                                              5

201
      RDFNEGQSAP ASHLIRVEGN NLSQYVDDPV TGRQSVVVPY EPPQVGTEFT
      RCSDSDGLAP PQHLIRVEGN LRVEYLDDRN TFRHSVVVPY EPPEVGSDCT
      181    5                                          6

251
      TILYNFMCNS SCMGGMNRRP ILTIITLEMR DGQVLGRRSF EGRICACPGR
      TIHYNYMCNS SCMGGMNRRP ILTIITLEDS SGNLLGRNSF EVRVCACPGR
      231                              8       7

301
      DRKADEDHYR EQQALNESSA KNGAASKRAF KQSPPAVPAL GAGVKKRRHG
      DRRTEEENLR KKGEPHHELP ..PGSTKRAL PNNTSSSPQ. ...PKKKPL.
      281    9                    8                       10

351
      DEDTYYLQVR GRENFEILMK LKESLEIMEL VPQPLVDSYR QQQQLLQRPS
      DGEYFTLQIR GRERFEMFRE LNEALELKDA QAGKEPGGSR AHSSHLKSKK
      324    9                                            10  11

401
      RLPPPYGPV LSPMNKVHGG MNKLPSVNQL VGQPPPHSSA ATPNLGPVGP
      .GPSTSRHKK L..MFKTEGP DSD
      374                    393                          12

451
      GMLNNHGHAV PANGEMSSSH SAQSMVSGSH CTPPPPYHAD PSLVSFLTGL
                                13
501
      GCPNCIEYFT SQGLQSIYHL QNLTIEDLGA LKIPEQYRMT IWRGLQDLKQ 551                                                      600
      GHDYSTAQQL LRSSNAATIS IGGSGELQRQ RVMEAVHFRV RHTITIPNRG 601                                              636
      GPGGGPDEWA DFGFDLPDCK ARKQPIKEEF TEAEIH
```

*FIG. 1A*

Human p73α/β

```
      451
α   GMLNNHGHAV PANGEMSSSH SAQSMVSGSH CTPPPPYHAD PSLVSFLTGL
β   GMLNNHGHAV PANGEMSSSH SAQSMVSGSH CTPPPPYHAD PSLVRTWGP*
```

FIG. 1B

Human p73α/Squid p53

```
      419
Hu  GGMNKLPSVN QLVGQPPHS  SAATPNLGPV GPGMLNNHGH AVPANGEMSS
Sq  GRLTSLPSSS SNGSQDGSRS STAFSTSDSS QVNSSQNNIQ MV. NGQV..
    396

Hu  SHSAQSMVSG SHCTPPPPYH ADPSLVSFLT GLGCPNCIEY FTSQGLQSIY
Sq  PHEEETPVTK CEPT...... .ENTIAQWLT KLGLQAVIDN FQQKGLHNMF

Hu  HLQNLTIEDL GALKIPEQYR MTIWRGLQDL KQGHDYSTAQ QLLR..SSNA
Sq  QLDEFILEDL QSMRIGTGHR NKIWKSLLDY RRLLSSGTES QAIQHAASNA

Hu  ATISIGGSGE LQRQRVMEAV HFRVRHTITI PNRGGPGGGP DEWADFGFDL
Sq  STLSVGSQNS YCPG.FYEVT RYTYKHTISY L
                                   564
           636
Hu  PDCKARKQPI KEEFTEAEIH
```

FIG. 1C

FIG. 2C
FIG. 2B
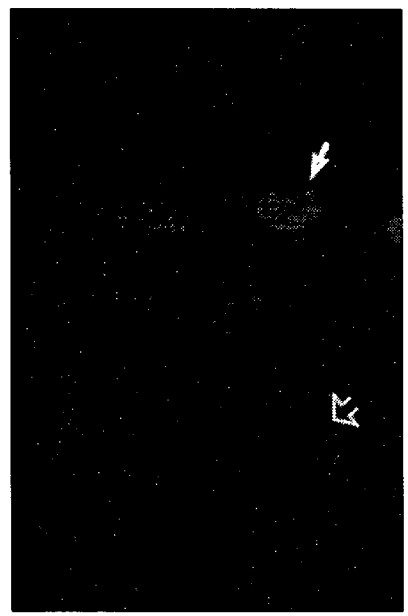
FIG. 2E
FIG. 2D

VECTOR

NBS-1β

NBS-1β 292

NBS-1α

NBS-1α 292

HOECHST

HOECHST

TUNEL

TUNEL

α-p53

α-HA

CONTROL LYSATE

E6 LYSATE

METHODS OF TREATMENT USING NBS-1, ANTIBODIES AND PROTEINS THERETO, AND USES OF THE ANTIBODIES

CROSS-REFERENCE TO RELATED APPLICATION

This Divisional Application claims the benefit under 35 U.S.C. §120 of U.S. Ser. No. 09/081,975, May 12, 1998 now U.S. Pat. No. 6,451,979, which claims the benefit under 35 U.S.C. § 119(e) of U.S. Provisional Application No. 60/046,207, filed May 12, 1997.

The present invention is directed to NBS-1 antibodies, and methods of using NBS-1 to suppress p53 directed growth.

BACKGROUND OF THE INVENTION p53 is the most frequently mutated tumor suppressor protein identified to date in human cancers.(Levine A J, et al., *Nature* 351:453-456 (1991); Hollstein M, et al, *Science* 253: 49-53 (1991)). The ability of p53 to negatively regulate cell growth is due, at least in part, to its ability to bind to specific DNA sequences and activate the transcription of target genes such as p21$^{Waf1}$/Cip1 (Haffer R & Oren M. *Curr. Opin. Genet. Dev.* 5:84-90 (1995)). Recently, a gene was identified which encodes a protein having a deduced amino acid sequence showing varying levels of homology to certain p53 domains, for example, p53 residues implicated in sequence specific direct DNA binding are conserved in this protein (*Science* 256:827-829 (1992)).

This gene, called NSB-1 (sometimes also called p73), maps to chromosome 1p36, a region which is frequently deleted in neuroblastomas (Versteeg R, et al., *Eur J Cancer* 31A:538-41 (1995)). See FIG. 1A. Wild type NSB-1 mRNA is not detectable in these tumors. The protein shows 29% identity with p53 amino acids 1-45 (the transactivation domain) and 63% identity with p53 amino acids 113-290 (the DNA binding domain) and 38% identity with p53 amino acids 319-363 (the p53 oligomerization domain). (FIG. 1A and 1C) Additionally, it has a sequence similar to p53's MDM2 binding domain of TFSDLW (SEQ ID NO:1), namely TFEDLW (SEQ ID NO:2). Although the homology between its N terminus and p53 is not as strong as the above-mentioned homology, there are also residues corresponding to amino acid residues in p53 that are frequently mutated which have been shown to be required for sequence specific DNA recognition by p53 . Namely R175,G245, R248, R249, R273 and R282. There is no significant homology at the carboxy terminal (amino acid residues 364-393). Splice variants of NBS-1 at the carboxy terminus result in two different isoforms referred to as α and β (see FIGS. 1A and B). In addition, other isoforms have been identified.

Surprisingly, despite the homology between the two proteins in the core area where p53 binds to SV40 large T antigen, whereas p53 strongly interacts with SV40 large antigen, NSB-1 does not. For example, in the yeast 2-hybrid system, when p53 is used as the "bait" molecule strong interactions with p53 and SV40T large T antigen are shown (FIG. 1D) but not between NBS-1 and SV40 large T antigen.

In view of the strong correlation between mutations in p53, inactivation of p53 and cancer tumors, it would be important to have a means to supplement p53 function and/or replace p53 function.

Similarly, in view of the correlation between defects in 1p36 chromosomal deletions and neuroblastomas it would be useful to have means for detecting or monitoring the level of that NBS-1 gene product. We report that NBS-1 can activate the transcription of p53 responsive genes and can inhibit cell growth in a p53-like manner.

SUMMARY OF INVENTION

We have now discovered that NBS-1 can activate the transcription of p53 responsive genes and can inhibit cell growth in a p53 -like manner.

For example, one can treat a subject having a p53 dependent tumor by determining the level of NBS-1 in the tumor cells, and comparing it to a corresponding non-malignant (normal) cell. If the level of NBS-1 in the tumor cell is not elevated, i.e., corresponding to or below the NBS-1 level in a normal cell, one can increase the level of NBS-1 in that cell. An alternative is to compare the NBS-1 level with the p53 level in the tumor cell. If the NBS-1 level is 10% or less, one can elevate the NBS-1 level. One preferred way of increasing NSB-1 levels is by transfecting the tumor cell with a vector containing a gene encoding NBS-1. Preferably, the NBS-1 gene is under the control of a powerful promoter. The NBS-1 then acts to reduce unchecked growth, for example, by negatively regulating a p53 response promoter.

BRIEF DESCRIPTION OF THE DRAWINGS

FIGS. 1A-1D compare NSB-1 (p73) with a number of other genes.

FIG. 1A shows the amino acid sequence of NBS-1α (SEQ ID NO:3) (and implicitly NSB-1β) in comparison to p53 (SEQ ID NO:4). Identities are enclosed in shaded boxes, p53 residues frequently mutated in tumors are shown in bold. Identity and position of introns are shown.

FIG. 1B compares the C-terminal sequence of NSB-1α (SEQ ID NO:5) and NBS-1β (SEQ ID NO:6) and shows that NSB-1β lacks exon 13.

FIG. 1C shows homology between a C-terminal portion of NBS-1α (amino acid residues 419-636 of SEQ ID NO:3) and a C-terminal portion of a squid p53-like protein (SEQ ID NO:7).

FIG. 1D shows yeast two hybrid interaction assays involving NBS-1α, p53 and SV40 large T antigen (ordinate) relative to β-galactosidase activity of p53-p53 interactions.

FIGS. 2A-2I show expression and subcellular localization of NBS-1. FIG. 2A shows anti-HA western blot of whole cell extracts (lanes 1-5) or of anti-HA immunoprecipitates (lanes 6-10) following transfection of SAOS2 osteogenic sarcoma cells with plasmids encoding the indicated proteins. FIGS. 2B-2I show anti-HA immunofluorescence (FIGS. 2B, 2D, 2F, and 2H) and Hoechst dye staining (FIGS. 2C, 2E, 2G, and 2I)) of BHK cells producing the indicated proteins. Examples of transfected and untransfected cells are shown by closed and open arrows, respectively.

FIG. 3A shows CAT assay of SAOS2 cells transfected with reporter plasmids containing either the β-globin promoter (β-globin CAT) or a minimal promoter consisting of two 53 binding sites upstream of a TATA box (2XRGC-CAT) along with p53 or NBS-1 expression plasmids, as indicated. FIG. 3B shows luciferase assay of SAOS2 cells transfected with reporter plasmids containing an ~2.7 kB p21 genomic clone spanning the p21 promoter (p21 wt) or a deletion mutant thereof lacking its p53 binding sites (del 8), along with p53 or NBS-1 expression plasmids, as indicated. Shown are luciferase values corrected for transfection efficiency. Error bars indicate 1 standard error of the mean.

FIGS. 4A-E show colony suppression by wild-type NBS-1 isoforms: Vector (FIG. 4A) NSB-1β (FIG. 4B), NBS-1α (FIG. 4C), NSB-1β292 (FIG. 4D), and NSB-1α292 (FIG. 4E). FIG. 4C shows Immunofluorescence and TUNEL analysis of BHK cells transfected with p53 (FIGS. 4F, 4G and 4H) or NSB-1α (FIGS. 4I, 4J and 4K) expression plasmids.

FIG. 6A are immunoprecipitates showing the interaction between NBS-1α and hMDM2. Anti-HA western blot of anti-HA immunoprecipitates (left 7 lanes) or anti-MDM2 immunoprecipitates (right 5 lanes) following transfection of SAOS2 cells with plasmids encoding the indicated proteins.

FIG. 6B is a schematic showing NBS-1α is repressed by hMDM2. SAOS2 cells were transfected with the indicated plasmids and CAT assays were performed on the transfectants. Values were normalized to βgal expression, and activity of wild-type p53 and NBS-1α alone were set to 100%.

FIG. 7A are immunoprecipitates that show that NBS-1α interacts with at least one p53 mutant. Anti-HA western blot of anti-HA immunoprecipitates (left 7 lanes) or anti-p53 immunoprecipitates (right 7 lanes) following transfection of SAOS2 cells with plasmids encoding the indicated proteins.

FIG. 7B are immunoprecipitates showing NBS-1α interacts with at least one p53 mutant. Anti-p53 western blot of anti-HA immunoprecipitates (left 7 lanes) or anti-p53 immunoprecipitates (right 7 lanes) following transfection of SAOS2 cells with plasmids encoding the indicated proteins.

FIG. 7C shows repression of both wild-type p53 and NBS-1α by dominant negative p53 143. Luciferase assays were done on SAOS2 cells transfected with either p53, NBS-1α and increasing amounts of p53 143. Activity of p53 and NBS-1α were set at 100%. All values are normalized to βgal expression.

FIG. 8A are immunoprecipitates showing SV40 large T antigen does not bind to NBS-1. Anti-HA western blot of anti-HA immunoprecipitates (lanes 1-5) or anti-T antigen immunoprecipitate (lanes 6-10) following transfection of COS cells with plasmids encoding the indicated plasmids.

FIG. 8B shows NBS-1α is not repressed by SV40 large T antigen. CAT assay on SAOS2 cells transfected with β-globin CAT reporter along with the indicator plasmid. Values were normalized to βgal expression and the levels of p53 and NBS-1α transactivation are set to 100%.

FIG. 10A is a schematic of the vector used to prepare antibodies. A segment from the 5' BamH1 site (1138) to the 3' Mun1 site (1905) was used and placed in pGex2T vector.

FIG. 10B shows NSB-1 expression in COS and SK-N-AS cell lines. Immunoprecipitation was performed on host cell extracts from either COS (left) or SK-N-AS (right) cells using indicated monoclonal antibodies. Immunoprecipitated material was separated electrophoretically, transferred to nylon membrane and blotted using a monoclonal antibody which recognizes both α and β isoforms. NS=nonspecific band. IgH=immunoglobulin heavy chain.

FIG. 10C are immunoprecipitates showing NBS-1 expression in IMR32 and SK-N-SH cells. Immunoprecipitation was performed on whole cell extracts from either IMR32 (left) or SK-N-SH (right) cells using indicated monoclonal antibodies. Immunoprecipitated material was separated electrophoretically, transferred to nylon membrane and blotted with a monoclonal antibody which recognizes both α and β and NBS isoforms. Abbreviations are as above.

DETAILED DESCRIPTION OF THE INVENTION

Figure 1D:
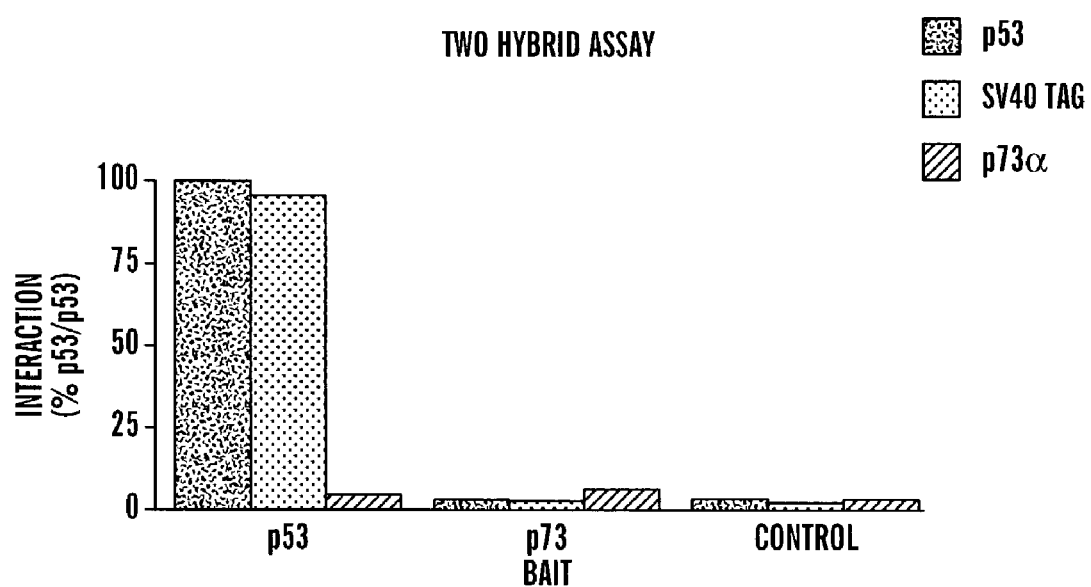

We have found that in many cells the NBS-1 gene is either dormant or expressing gene product at extremely low levels. We have discovered that the NBS-1 protein can augment or complement p53 function in a number of areas.

One problem in using gene therapy where there is a p53-dependent defect is that the typical approaching, enhancing p53 expression, frequently does not work because there is a feedback mechanism keeping p53 in check or inactivating p53. For example, enhancing expression of p53 is useless in a cell where there is a mutation in the p53 gene because all it ends up doing is increasing levels of mutant p53. On the other hand, in many cells the NBS-1 gene is dormant. Thus, being able to turn this gene on or introducing this gene into a cell provides an alternative mechanism of restoring p53-like function, that avoids the mechanisms directly affecting p53. For example, NBS-1 can be used to turn on p53 responsive transcription. It can be used to result in p53 inhibition and p53 induced apotosis.

We have found that using p53 responsive sites (e.g. RGC) in a promoter operably linked to a gene, e.g. NBS-1, keeps the linked gene under the transcriptional control of the promoter, but that the p53 responsive sites are responsive to suppression by NSB-1, as well as p53. For example, a 2XRGC-CAT construct responds to NBS-1 as well as p53. This confirms that NBS-1 can be used to induce p53-like growth suppression. It also has an effect on inducing apotosis. One can artificially create such promoters or use naturally responsive promoters such as the p21 promoter.

Thus, in one preferred embodiment one can determine whether a particular tumor is appropriate for induction or enhancement of NBS-1 expression. First, one determines the level of NBS-1 expression in that cell as compared to the corresponding non-malignantly transformed cell. This can be done, for example, by using an antibody that specifically recognizes NSB-1. This permits selection of target cells where NBS-1 is normally expressed at extremely low levels or not at all. For example, the level of NBS-1 expression can be compared to the level of p53 expression. Preferably, the level of expression is no more than 10% that of NBS-1 p53 expression. More preferably, it is less than 5% of the level of p53. Still more preferably, it is less than 1% of the level of p53. These target cells can then have their NBS-1 expression "turned on" or enhanced. This can be done by a variety of means known in the art. For example, one can transform a target cell with a vector encoding NBS-1. Preferably the vector is operably linked to a high expression promoter. The use of enhancers and other elements to increase levels of expression can also be used. Alternatively, one can add a compound that enhances expression of native NBS-1 in that cell. Preferably, the compound is a small molecule. Similarly, because of the relationship between NBS-1 function and p53 it may be possible by using p53 to augment NBS-1 function in cells where NBS-1 is misfunctioning or being deleted.

In another embodiment, the NBS-1 antibodies can be used to select cells either not expressing NBS-1 or expressing low levels of NBS-1. These cell lines can then be used in assays to discover other compounds that enhance NBS-1 expression. For example, one can add a test compound to such a cell and then measure the level of NBS-1 expression using these antibodies. In addition to using antibodies, one can look at levels of transcript or the DNA itself by standard techniques. In some instances one can use NBS-1 as a type of p53 agonist. For example, there are functional portions of NBS-1 that appear to mimic certain p53 domains. For example, NBS-1 has a number of domains that can complement or augment a specific p53 function, such as activating p53 responsive transcription elements. However, there are areas where despite apparent homology, the two molecules act quite different.

Figure 8B:
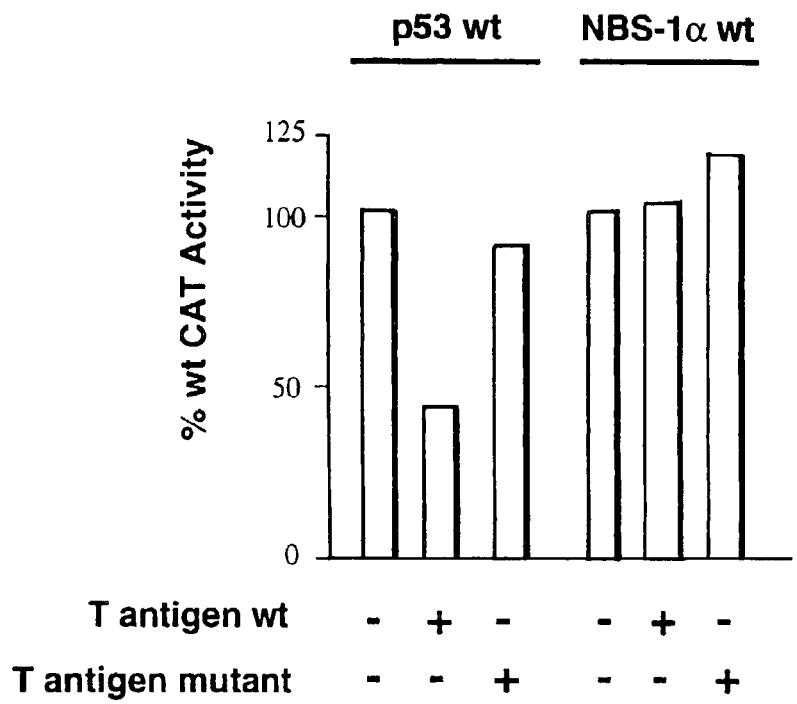
FIGS. 8A and 8B show interactions between SV40 large T antigen and NBS-1.
Figure 8A:
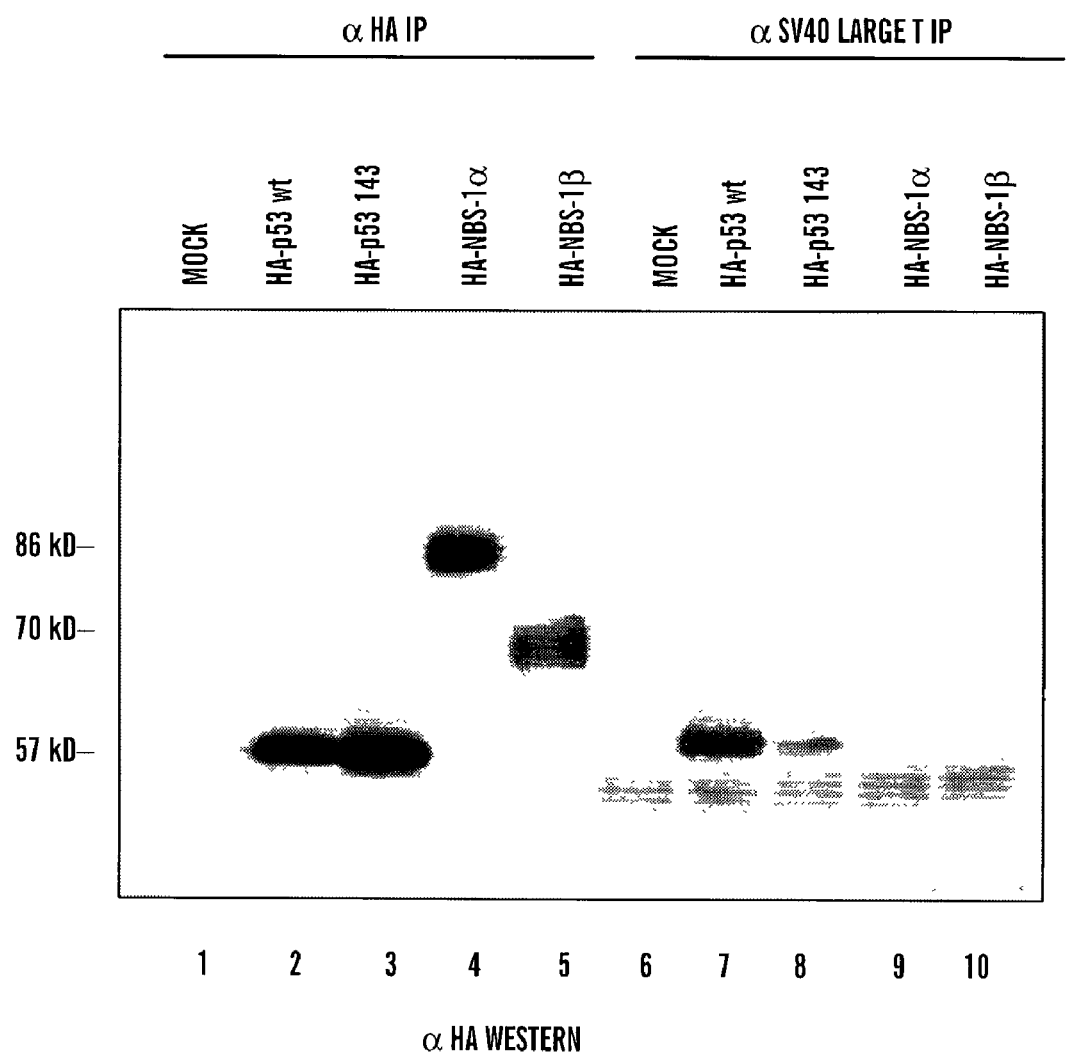

NBS-1 and p53 share significant homology at the core domain required for SV40 large T antigen interaction. Yet, NBS-1 does not interact with SV40 T large antigen. NBS-1, like p53 was also first identified in COS cells, which overexpress SV40 large T antigen. It was known that SV40 large T antigen stabilized level of p53 protein, and likely accounts for the fact that p53 was more easily detectable in this cell line than others. Thus, one would have expected NBS-1 to interact similarly. A series of in-vitro and in-vivo experiments were performed with NBS-1. COS cells were transfected with mammalian expression plasmids encoding HA-tagged versions of either p53 wild type, p53V143A, NBS-1α or NSB-1β. 48 hours following transfection, cell lysates were prepared and immunoprecipitated with either anti-HA antibody (FIG. 8A, lanes 1-5), or anti-SV40 large T antigen antibody (FIG. 8A, lanes 6-10). Bound proteins were analyzed by protein gel electrophoresis followed by western blotting with an anti-HA antibody. As expected, wild type p53 co-immunoprecipitated with endogenous SV40 large T antigen (compare lane 2 with 7). Mutant p53 was greatly reduced in its ability to interact with SV40 large T antigen (compare lane 3 with lane 8). The surprising result was that neither NSB-1α or NSB-1β could interact to any discernable extent with SV40 large T antigen (compare lane 4 with lane 9, and lane 5 with lane 10). This result was confirmed by in vitro assays in which baculovirus produced SV40 T antigen is incubated with reticulocyte produced NBS-1, immunoprecipitated with anti-SV40 large T antigen antibody, and analyzed by protein gel electrophoresis. Under conditions where reticulocyte produced wild type p53 is seen to associate with baculovirus large T antigen, no such association is seen with either isoform of NBS-1.

Wild type, but not mutant SV40 large T antigen can repress wild type p53 activity, which is set at 100%. (See FIG. 8B) In contrast, neither wild type nor mutant SV40 large T antigen has any appreciable effect on NBS-1α transcriptional activity.

Another small DNA oncoprotein which inactivates p53 is the human papilloma virus E6 protein (Scheffner, et al., 1990).

Figure 9A:
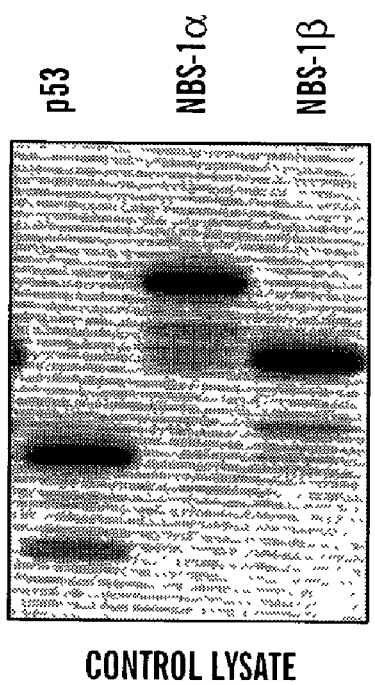
FIGS. 9A and 9B show NBS-1 is not destroyed by the adenovirus E6 protein. Reticulocyte-translated p53, NSB-1α or NBS-β were incubated with either control lysate (FIG. 9A) or GST-E6 lysate (FIG. 9B). After a three-hour incubation, the reactions were separated by electrophoresis.
Figure 9B:
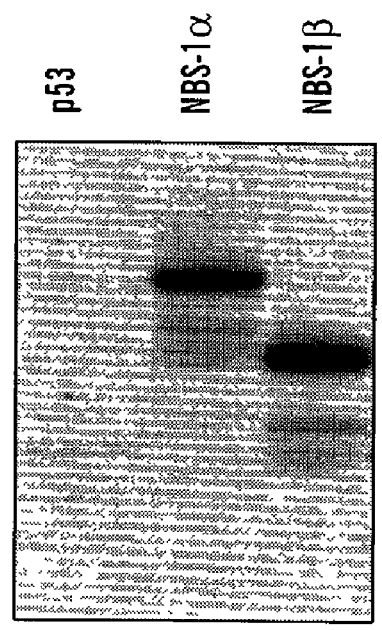

Incubation of p53 with GST-E6 resulted in near complete destruction of the input protein (Compare lanes 1 of FIGS. 9A and 9B). Incubation with GST-E6 did not, however, result in any degradation whatsoever of NBS-1α or NBS-1β (Compare lanes 2 and lanes 3 of FIGS. 9A and 9B).

There are domains where certain p53 function appear to be mimicked and one can use segments containing such domains or nucleic acid encoding such segments to result in certain activity.

Figure 5:
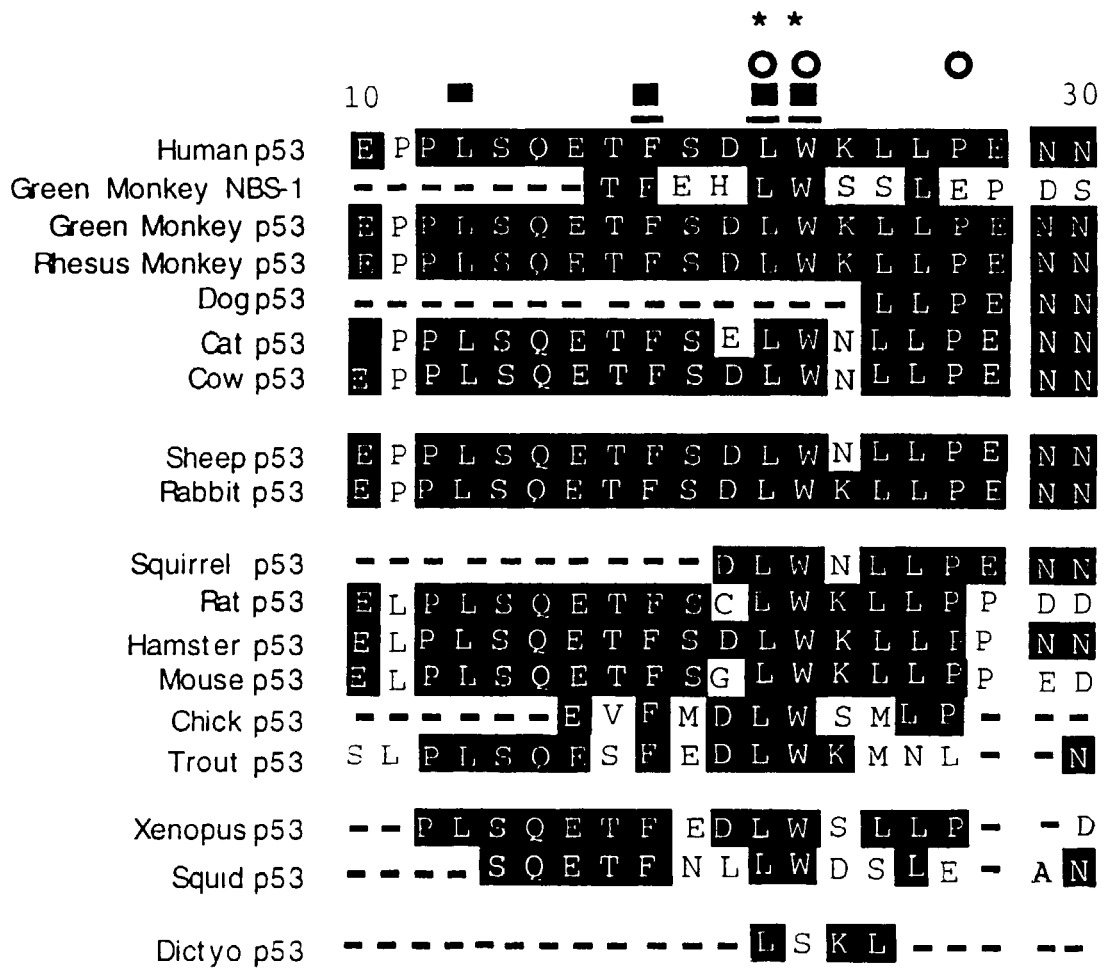
FIG. 5 is a comparison of amino acid sequences involved in interaction between p53 and MDM2,E1B 55KDa and TBP. A ■ equals MDM2 interaction, a ○ equals EIB 55KDa interaction. A ★ equals TBP interaction. A ■ equals MDM2 interaction confirmed in crystal structure. The amino acid sequences shown are from Human p53 (SEQ ID NO:8); Green Monkey NSB-1 (SEQ ID NO:9); Green Monkey p53 (SEQ ID NO:10); Rhesus Monkey p53 (SEQ ID NO:11); Dog p53 (SEQ ID NO:12); Cat p53 (SEQ ID NO:13); Cow p53 (SEQ ID NO:14); Sheep p53 (SEQ ID NO:15); Rabbit p53 (SEQ ID NO:16); Squirrel p53 (SEQ ID NO:17); Rat p53 (SEQ ID NO:18); Hamster p53 (SEQ ID NO:19); Mouse p53 (SEQ ID NO:20); Chick p53 (SEQ ID NO:21); Trout p53 (SEQ ID NO:22); Xenopus p53 (SEQ ID NO:23); Squid p53 (SEQ ID NO:24); and Dictyo p53 (SEQ ID NO:25).
Figure 6A:
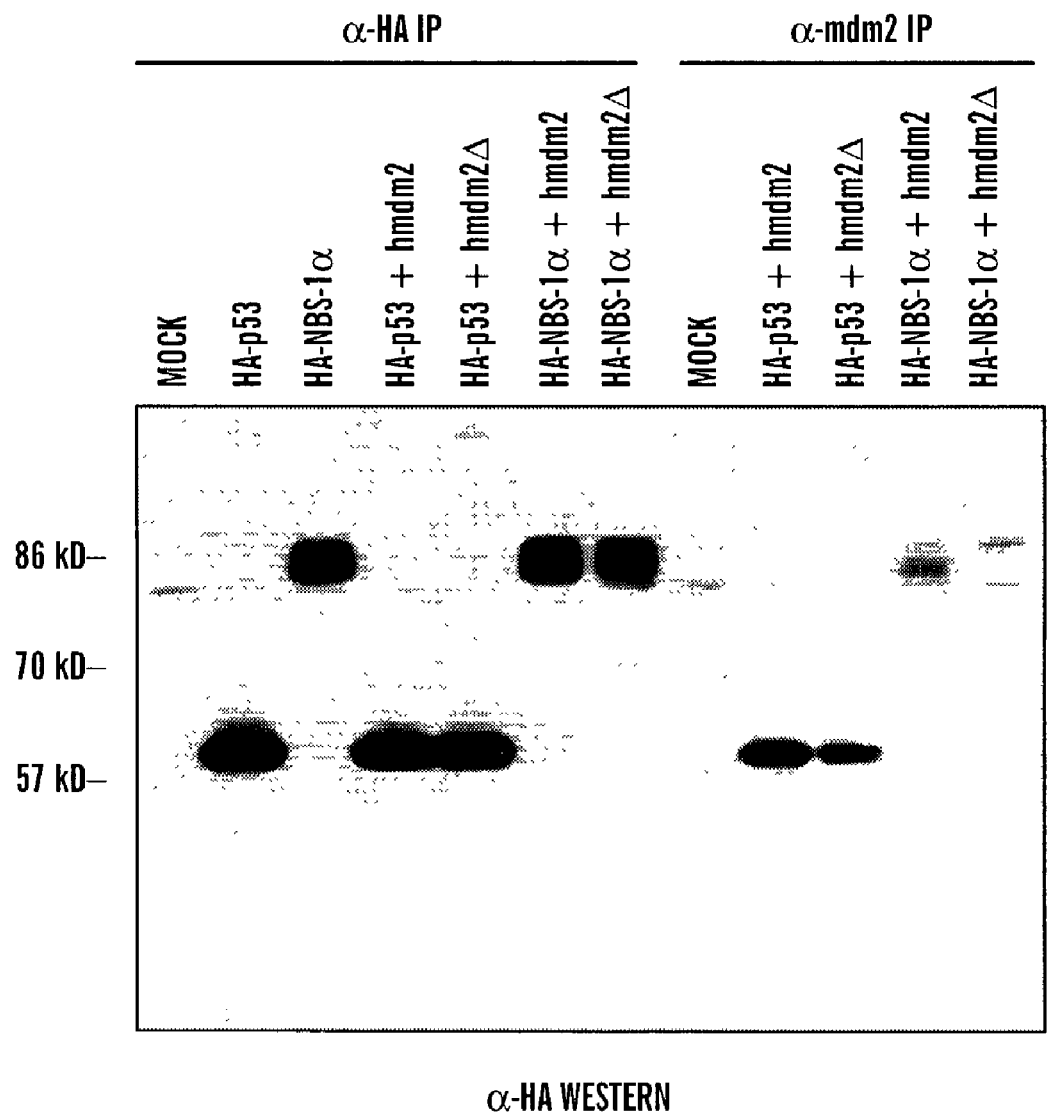
FIGS. 6A and 6B show interactions between NBS-1α and hMDM2.

For example, p53 can bind to the MDM2 protein, in a relationship that can be described as a regulatory loop, whereby p53 positively regulates MDM2 and MDM2 negatively regulates p53. The three amino acids in p53 found to make direct contact with MDM, Phe 19, Leu 22 and Trp 23, are identical in NSB-1 (Kussie, et al., 1996), (FIG. 5). We have found that NSB-1 can physically interact with hMDM2 in a similar loop. Thus, MDM2 can analogously repress NBS-1 mediated transactivation. For example, SAOS2 osteosarcoma cells were transfected with mammalian expression plasmids encoding HA-tagged p53, HA-tagged NBS-1α, with or without expression plasmids encoding hMDM2, or a mutant of MDM2, MDM2 delXX. This MDM2 mutant was previously shown not to interact with p53. Cells were lysed 48 hours following transfection, and each lysate was immunoprecipitated either with an anti-HA or anti-MDM2 antibody. Bound proteins were analyzed by protein gel electrophoresis followed by anti-HA western blot analysis. FIG. 6A (lanes 1-7) indicates the level of expression of the HA-tagged p53 and NBS-1α proteins. FIG. 6A (lanes 8-12) shows the association of HA-tagged p53 or NBS-1α with MDM2 or MDM2XX. A large portion of expressed p53 interacts with wild type MDM2 (compare lane 4 to lane 9). A much reduced amount of p53 is seen to interact with mutant MDM2 (compare lane 5 to lane 10). Comparable amounts of wild-type and mutant MDM2 were expressed in all cases as assayed by anti-MDM2 western blot (data not shown). A small portion of expressed NBS-1α was seen to interact with wild type MDM2 (compare lane 6 to lane 11). Significantly an interaction between NBS-1α, and between a mutant of NBS-1 DXX, which has the putative MDM2 interaction domain deleted, and wild type MDM2 was not detected (data not shown). Therefore, although the stoichiometry of interaction between NBS-1α and MDM2 is different than that of p53/MDM2, the genetics of the interaction seems similar. In this manner, NBS-1 can be used as a decoy for p53. In this way one can use NSB-1-MDM2 interaction to limit MDM2-p53 interactions.

Figure 6B:
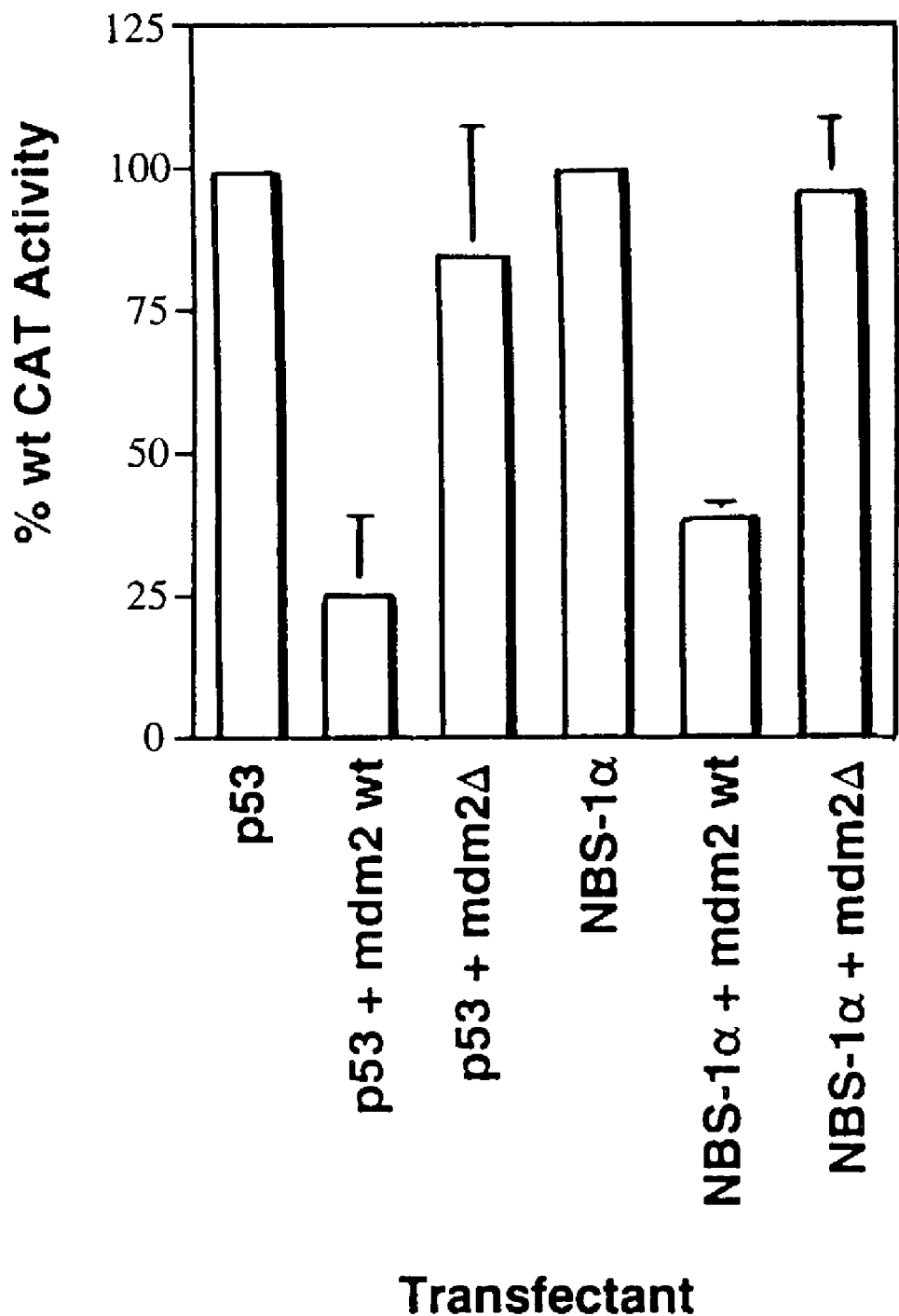

We have shown that using SAOS2 cells, MDM2 can also repress NBS-1. These cells are transfected with mammalian expression plasmids encoding either p53 or NBS-1α, with or without plasmids encoding wild type or mutant hMDM2, and at a second site p53 promoter-CAT reporter. Wild type p53 transactivation is substantially repressed by wild-type, but not mutant hMDM2 (FIG. 6B). Surprisingly, NBS-1α transactivation was repressed to an almost identical extent as p53 by wild type, but not mutant hMDM2. Therefore, although the affinity of NSB-1/MDM2 interaction seemed much weaker than p53/MDM2, both p53 and NSB-1 were repressed to a similar extent by equal amounts of MDM2.

Wild type p53 can oligomerize with mutant forms of p53, resulting in repression of transactivation by wild type. Mutant p53 can also oligomerize with NBS-1 and repress NBS-1 transactivation. For example, SAOS2 cells were transfected with mammalian expression plasmids encoding HA-tagged NBS-1α along with untagged versions of either wild type or mutant p53.

48 hours following transfection, cells were lysed and immunoprecipitated with either an anti-HA antibody (FIG.

Figure 7A:
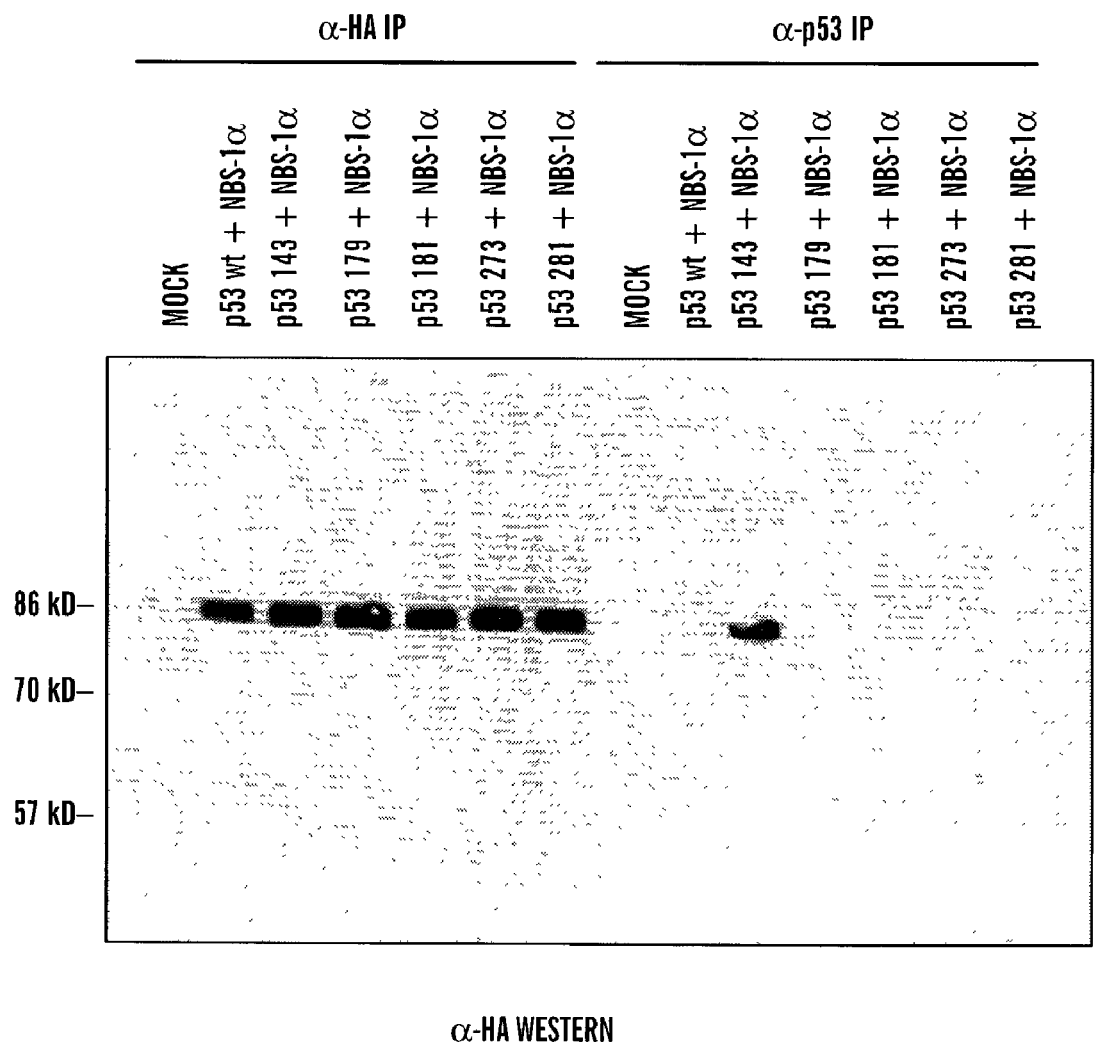
FIGS. 7A-7C show interaction between NBS-1α and p53 or p53 mutants.
Figure 7B:
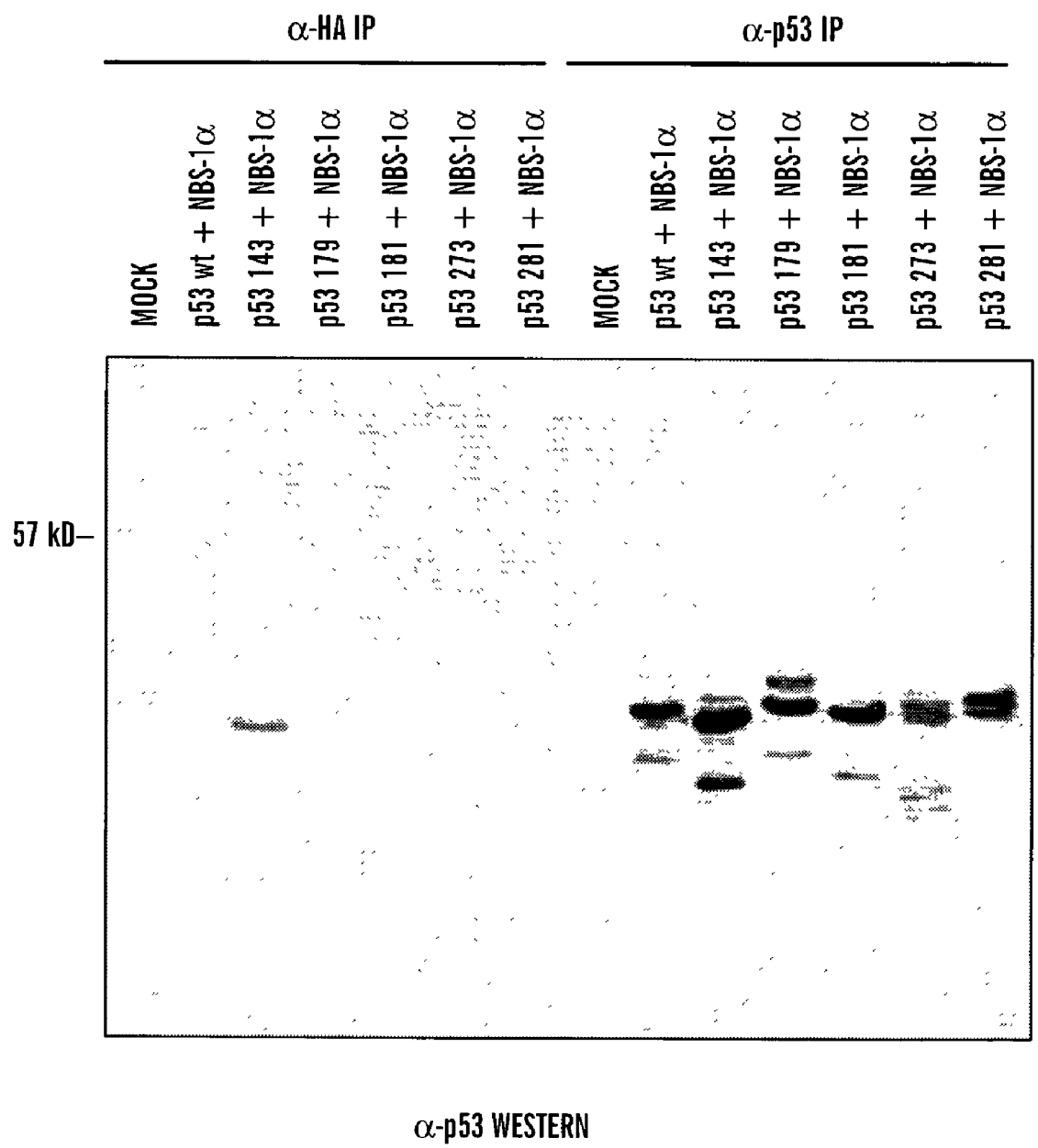

7A, lanes 1-7), or an anti-p53 antibody (FIG. 7A, lanes 8-14). Bound proteins were analyzed by protein gel electrophoresis followed by an anti-HA western blot. As can be seen in FIG. 7A, comparable levels of NBS-1α were expressed in all cases (lanes 2-8). NBS-1α was co-immunoprecipitate with a mutant p53, p53V1r3A, but not wild-type p53 (compare lanes 3 with 10, and lanes 2 with 9). A weaker interaction was seen between NBS-1α and the mutant p53 179 (compare lane 4 with 11). The interaction between NBS-1α and p53V143A was also seen when assayed in the other direction. One half of the immunoprecipitated material used in FIG. 7A was separated by protein gel electrophoresis, but in this case the western blot was performed using an anti-p53 antibody. As can be seen in FIG. 7B, comparable levels of p53 wild-type and mutant proteins were expressed in transfection, although the pattern of modification appears slightly different (compare lanes 9-14). Importantly, the interaction between NBS-1α and p53V143A is again seen, (compare lane 10 with lane 3).

Figure 7C:
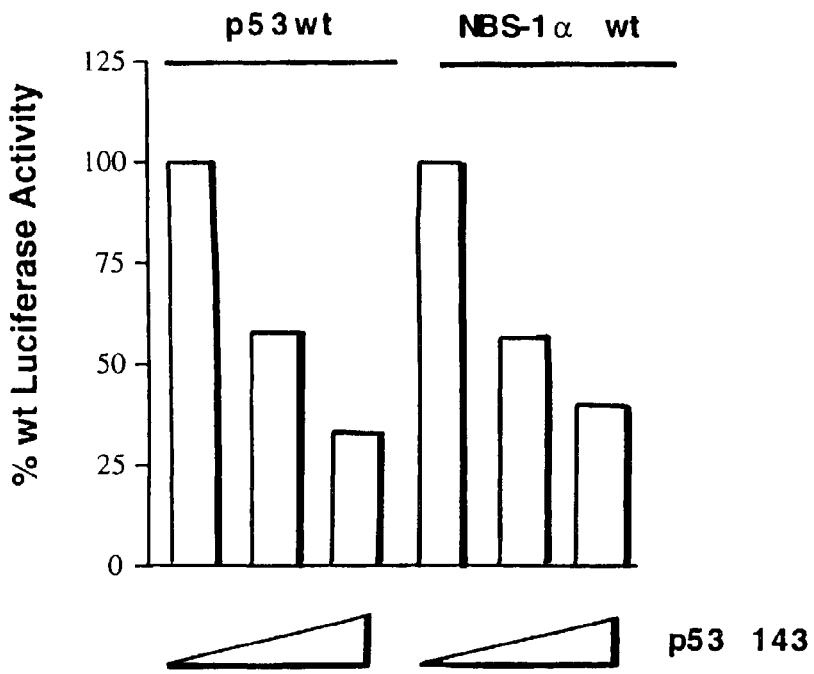

NBS-1α dependent transactivation could be repressed by a p53 repression mutant such as p53V143A. For example, SAOS2 cells were transfected with expression plasmids encoding either wild type NSB-1α or p53, a p53 responsive promoter-luciferase reporter and increasing amounts of p53V143A expression plasmid. The titration of increasing amounts of p53V143A leads to increased repression of p53-dependent transactivation (FIG. 7C). The same level of repression of NBS-1α-dependent transactivation was observed when increasing amounts of p53V143A was titrated in (FIG. 7C). Thus p53V143A seems to have the same dominant negative action over NBS-1α as it exerts over wild-type p53.

Figure 10A:
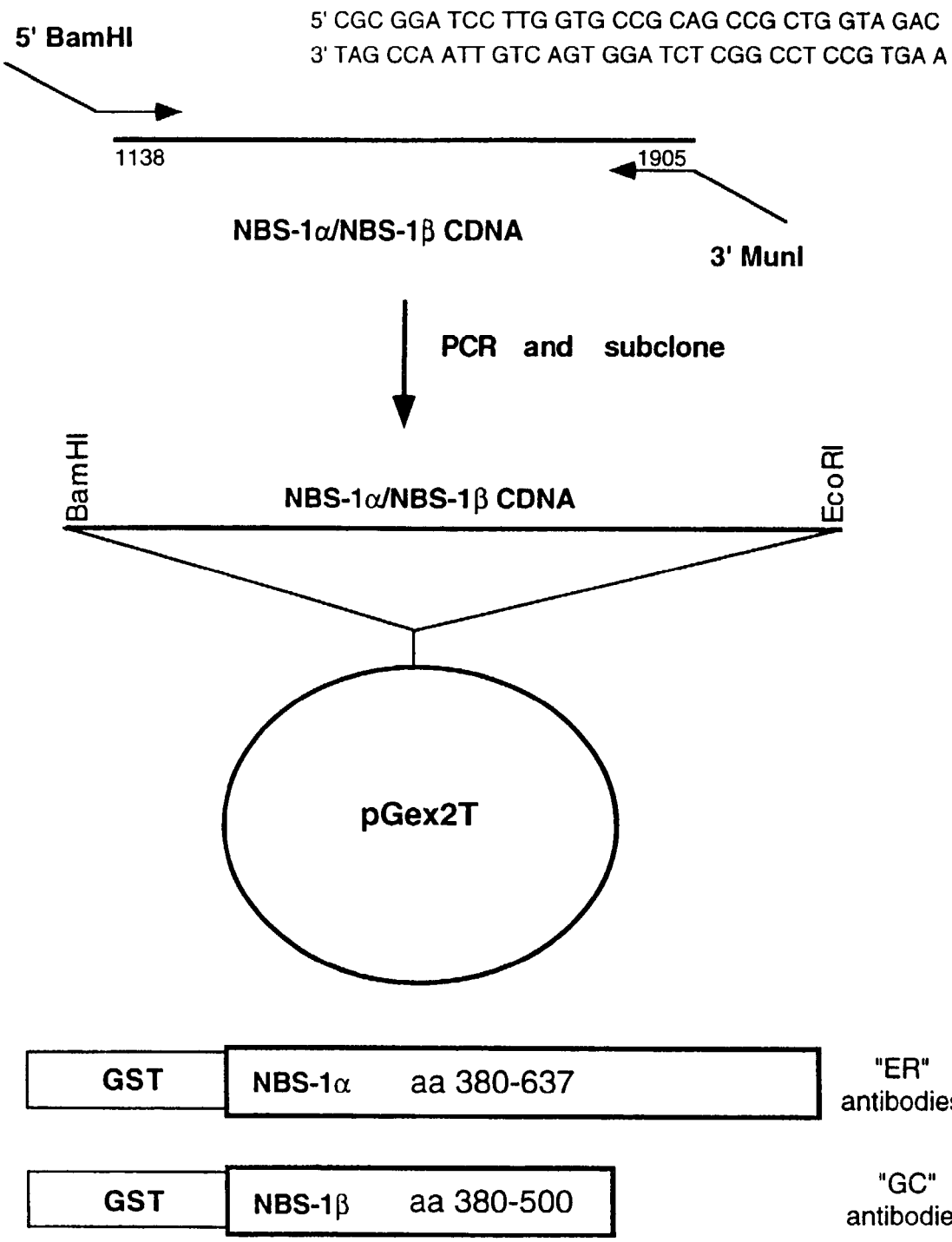
FIGS. 10A-10C show the preparation of a NBS-1 antibody and its use.
Figure 10B:
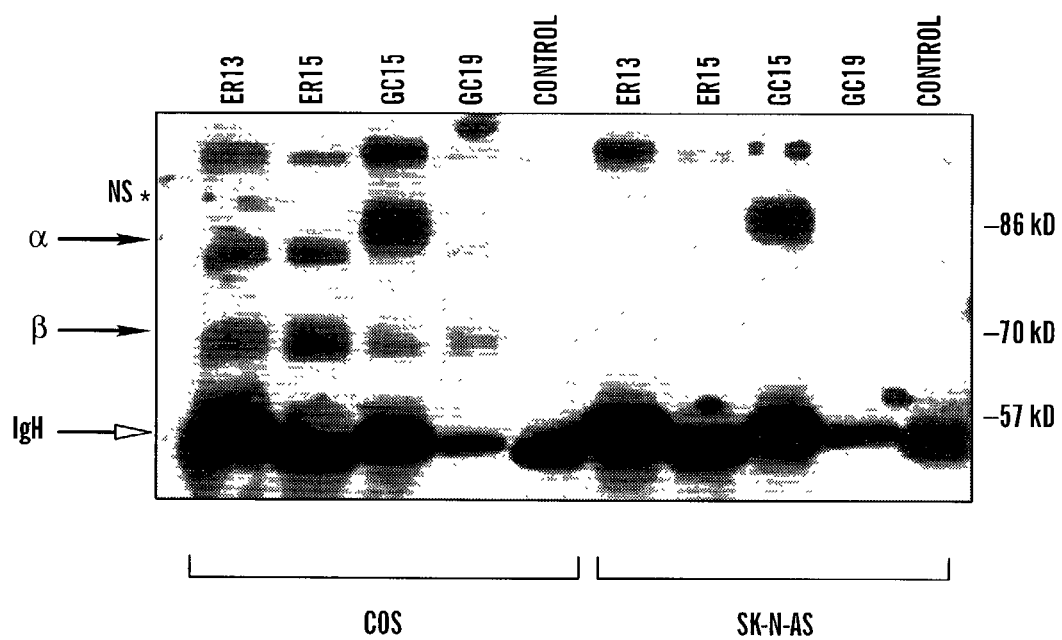
Figure 10C:
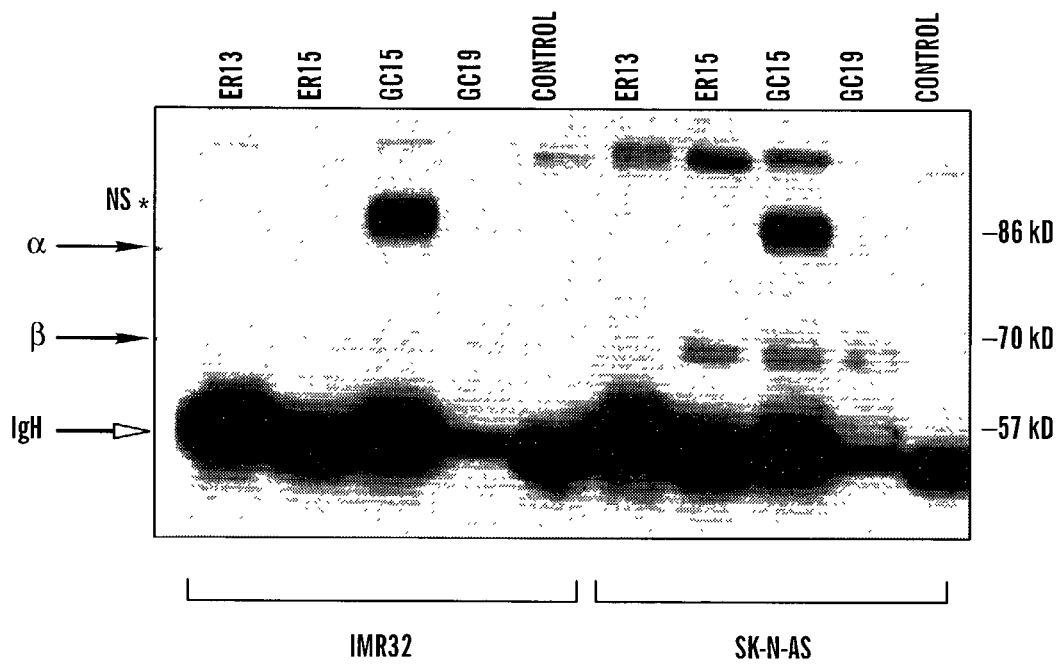

Monoclonal antibodies to NBS-1α and NBS-1β can be generated by injecting GST fusions of the C-terminus of either NBS-1α or NSB-1β into mice. These GST-fusions are represented graphically in FIG. 10A. COS cells were chosen as a positive control cell line for NBS-1 expression, since the original isolation of the NBS-1 isoforms came from a COS cell cDNA (Caput, personal communication). Subconfluent plates of either COS or NBS cell lines were lysed, and immunoprecipitated with one of four NBS-1 monoclonal antibodies. Bound proteins were analyzed by protein gel electrophoresis, followed by western blotting with an NBS-1 monoclonal which reacts with both isoforms. Immunoprecipitation of COS cells with NBS-1 monoclonal antibodies, but not with a control monoclonal, results in detection of both isoforms of NBS-1 (FIG. 6B, lanes 1-5, arrows labeled a and b). Note that immunoprecipitation with antibody GC15 results in a non-specific band at approximately the same molecular eight as NBS-1α (denoted by the arrow labeled NS, lanes 3 and 8, data not shown).

Using these antibodies NBS-1 expression can be monitored in a variety of cell lines. For example, in contrast to the COS cells there seems to be no expression of NBS-1α or NSB-1β in the NB cell line SK-N-AS (FIG. 6B, lanes 6-10). This is the cell line with the smallest characterized 1p365 deletion amongst NB cell lines. Two additional NB cell lines, IMR32 and SK-N-SH, were analyzed (FIG. 6C). As in FIG. 6B, subconfluent dishes of cells were lysed and immunoprecipitated with one of four NBS-1 monoclonal antibodies, or a control antibody. Bound proteins were separated by protein gel electrophoresis, followed by western blot analysis with an NBS-1 monoclonal which is reactive with both isoforms. Both cell lines showed a similar NBS-1 expression pattern (FIG. 6C). In either case, 3 out of 4 of the NBS-1 monoclonals immunoprecipitated NBS-1β, but not NBS-1α (FIG. 6C, lanes 2-4, 7-9).

As used herein, the term "antibodies" is meant to include monoclonal antibodies, polyclonal antibodies and antibodies prepared by recombinant nucleic acid techniques that are selectively reactive with polypeptides encoded by eukaryotic nucleotide sequences of the present invention. The term "selectively reactive" refers to those antibodies that preferentially react with one or more antigenic determinants of NBS-1. Antigenic determinants usually consist of chemically active surface groupings of molecules such as amino acids or sugar side chains and have specific three dimensional structural characteristics as well as specific charge characteristics. Antibodies can be used for diagnostic applications or for research purposes.

Antibodies can be prepared by means well known in the art. The term "antibodies" is meant to include monoclonal antibodies, polyclonal antibodies and antibodies prepared by recombinant nucleic acid techniques that are selectively reactive with a desired antigen such as NBS-1. Antigenic determinants usually consist of chemically active surface groupings of molecules such as amino acids or sugar side chains and have specific three dimensional structural characteristics as well as specific charge characteristics. Antibodies can be used for diagnostic applications or for research purposes.

For example, antibodies may be raised against amino-terminal (N-terminal) or carboxyl-terminal (C-terminal) peptides of a polypeptide. Most preferably, one selects the C-terminal.

One method is by using hybridoma mRNA or splenic mRNA as a template for PCR amplification of such genes [Huse, et al., *Science* 246:1276 (1989)]. For example, an NBS-1 antibody can be derived from murine monoclonal hybridomas [Richardson J. H., et al., *Proc Natl Acad Sci USA* Vol. 92:3137-3141 (1995); Biocca S., et al., *Biochem and Biophys Res Comm*, 197:422-427 (1993) Mhashilkar, A. M., et al., *EMBO J.* 14:1542-1551 (1995)]. These hybridomas provide a reliable source of well-characterized reagents for the construction of antibodies and are particularly useful when their epitope reactivity and affinity has been previously characterized. Another source for such construction includes the use of human monoclonal antibody producing cell lines. [Marasco, W. A., et al., *Proc Natl Acad Sci USA*, 90:7889-7893 (1993); Chen, S. Y., et al., *Proc Natl Acad Sci USA* 91:5932-5936 (1994)]. Another example includes the use of antibody phage display technology to construct new antibodies against different epitopes on a target molecule. [Burton, D. R., et al., *Proc Natl Acad Sci USA* 88:10134-10137 (1991); Hoogenboom H. R., et al., *Immunol Rev* 130:41-68 (1992); Winter G., et al., *Annu Rev Immunol* 12:433-455 (1994); Marks, J. D., et al., *J Biol Chem* 267:16007-16010 (1992); Nissim, A., et al., *EMBO J* 13:692-698 (1994); Vaughan T. J., et al., *Nature Bio* 14:309-314 (1996); Marks C., et al., *New Eng J Med* 335:730-733 (1996)]. For example, very large naive human sFv libraries have been and can be created to offer a large source or rearranged antibody genes against a plethora of target molecules. Smaller libraries can be constructed from individuals with autoimmune [Portolano S., et al., *J Immunol* 151:2839-2851 (1993); Barbas S. M., et al., *Proc Natl Acad Sci USA* 92:2529-2533 (1995)] or infectious diseases [Barbas C. F., et al., *Proc Natl Acad Sci USA* 89:9339-9343 (1992); Zebedee S. L., et al., *Proc Natl Acad Sci USA* 89:3175-3179 (1992)] in order to isolate disease specific antibodies.

Other sources include transgenic mice that contain a human immunoglobulin locus instead of the corresponding mouse locus as well as stable hybridomas that secrete human antigen-specific antibodies. [Lonberg, N., et al., *Nature* 368:856-859 (1994); Green, L. L., et al., *Nat Genet* 7:13-21

(1994)]. Such transgenic animals provide another source of human antibody genes through either conventional hybridoma technology or in combination with phage display technology. In vitro procedures to manipulate the affinity and fine specificity of the antigen binding site have been reported including repertoire cloning [Clackson, T., et al., *Nature* 352: 624-628 (1991); Marks, J. D., et al., *J Mol Biol* 222:581-597 (1991); Griffiths, A. D., et al., *EMBO J* 12:725-734 (1993)], in vitro affinity maturation [Marks, J. D., et al., *Biotech* 10:779-783 (1992); Gram H., et al., *Proc Natl Acad Sci USA* 89:3576-3580 (1992)], semi-synthetic libraries [Hoogenboom, H. R., supra; Barbas, C. F., supra; Akamatsu, Y., et al., *J Immunol* 151:4631-4659 (1993)] and guided selection [Jespers, L. S., et al., *Bio Tech* 12:899-903 (1994)]. Starting materials for these recombinant DNA based strategies include RNA from mouse spleens [Clackson, T., supra] and human peripheral blood lymphocytes [Portolano, S., et al., supra; Barbas, C. F., et al., supra; Marks, J. D., et al., supra; Barbas, C. F., et al., *Proc Natl Acad Sci USA* 88:7978-7982 (1991)] and lymphoid organs and bone marrow from HIV-1-infected donors [Burton, D. R., et al., supra; Barbas, C. F., et al., *Proc Natl Acad Sci USA* 89:9339-9343 (1992)].

Thus, one can readily screen an antibody to insure that it has a sufficient binding affinity for the antigen of interest. The binding affinity ($K_d$) should preferably be at least about $10^{-7}$ l/mol, more preferably at least about $10^{-8}$ l/mol.

For example, cDNA clone encoding NBS-1 or a fragment thereof may be expressed in a host using standard techniques such that 5-20% of the total protein that can be recovered from the host is the desired protein. Recovered proteins can be electrophoresed using PAGE and the appropriate protein band can be cut out of the gel. The desired protein sample can then be eluted from the gel slice and prepared for immunization. Alternatively, a protein of interest can be purified by using conventional methods such as, for example, ion exchange hydrophobic, size exclusion, or affinity chromatography.

Once the protein immunogen is prepared, mice can be immunized twice intraperitoneally with approximately 50 micrograms of protein immunogen per mouse. Sera from such immunized mice can be tested for antibody activity by immunohistology or immunocytology on any host system expressing such polypeptide and by ELISA with the expressed polypeptide. For immunohistology, active antibodies of the present invention can be identified using a biotin-conjugated anti-mouse immunoglobulin followed by avidin-peroxidase and a chromogenic peroxidase substrate. Preparations of such reagents are commercially available; for example, from Zymad Corp., San Francisco, Calif. Mice whose sera contain detectable active antibodies according to the invention can be sacrificed three days later and their spleens removed for fusion and hybridoma production. Positive supernatants of such hybridomas can be identified using the assays described above and by, for example, Western blot analysis.

To further improve the likelihood of producing an antibody, the amino acid sequence of polypeptides encoded by a eukaryotic nucleotide sequence of the present invention may be analyzed in order to identify portions of amino acid sequence which may be associated with increased immunogenicity. For example, polypeptide sequences may be subjected to computer analysis to identify potentially immunogenic surface epitopes. Such computer analysis can include generating plots of antigenic index, hydrophilicity, structural features such as amphophilic helices or amphophilic sheets and the like.

For preparation of monoclonal antibodies directed toward polypeptides encoded by a eukaryotic nucleotide sequence of the invention, any technique that provides for the production of antibody molecules by continuous cell lines may be used. For example, the hybridoma technique originally developed by Kohler and Milstein (Nature, 256:495-497, 1973), as well as the trioma technique, the human B-cell hybridoma technique (Kozbor et al., Immunology Today, 4:72), and the EBV-hybridoma technique to produce human monoclonal antibodies, and the like, are within the scope of the present invention. See, generally Larrick et al., U.S. Pat. No. 5,001,065 and references cited therein. Further, single-chain antibody (SCA) methods are also available to produce antibodies against polypeptides encoded by a eukaryotic nucleotide sequence of the invention (Ladner et al. U.S. Pat. Nos. 4,704,694 and 4,976,778).

Another method for preparing antibodies is by in vitro immunization techniques, such as using spleen cells, e.g., a culture of murine spleen cells, injecting an antigen, and then screening for an antibody produced to said antigen. With this method, as little as 0.1 micrograms of antigen can be used, although about 1 microgram/milliliter is preferred. For in vitro immunization, spleen cells are harvested, for example, mice spleen cells, and incubated at the desired amount, for example, $1 \times 10^7$ cells/milliliter, in medium plus with the desired antigen at a concentration typically around 1 microgram/milliliter. Thereafter, one of several adjuvants depending upon the results of the filter immunoplaque assay are added to the cell culture. These adjuvants include N-acetyl-muramyl-L-alanyl-D-isoglutamine [Boss, *Methods in Enzymology* 121:27-33 (1986)], Salmonella typhimurium mitogen [Technical Bulletin, Ribi ImmunoChem. Res. Inc., Hamilton, Mont.] or T-cell condition which can be produced by conventional techniques [See, Borrebaeck, C. A. K., *Mol. Immunol.* 21:841-845 (1984); Borrebaeck, C. A. K., *J. Immunol.* 136:3710-3715 (1986)] or obtained commercially, for example, from Hannah Biologics, Inc. or Ribi ImmunoChem. Research Inc. The spleen cells are incubated with the antigen for four days and then harvested.

Single cell suspensions of the in vitro immunized mouse spleen cells are then incubated, for example on antigen-nitrocellulose membranes in microfilter plates, such as those available from Millipore Corp. The antibodies produced are detected by using a label for the antibodies such as horseradish peroxidase-labeled second antibody, such as rabbit anti-mouse IgA, IgG, and IgM. In determining the isotype of the secreted antibodies, biotinylated rabbit anti-mouse heavy chain specific antibodies, such as from Zymed Lab., Inc. can be used followed by a horseradish peroxidase-avidin reagent, such as that available from Vector Lab.

The insoluble products of the enzymatic reaction are visualized as blue plaques on the membrane. These plaques are counted, for example, by using 25 times magnification. Nitrocellulose membrane of the microfilter plaques readily absorb a variety of antigens and the filtration unit used for the washing step is preferred because it facilitates the plaque assay.

One then screens the antibodies by standard techniques to find antibodies of interest. Cultures containing the antibodies of interest are grown and induced and the supernatants passed through a filter, for example, a 0.45 micromiter filter and then through a column, for example, an antigen affinity column or an anti-tag peptide column. The binding affinity is tested using a mini gel filtration technique. See, for example, Niedel, J., *Biol. Chem.* 256:9295 (1981). One can also use a second assay such as a radioimmunoassay using magnetic beads coupled with, for example, anti-rabbit IgG to separate free $^{125}$I-labeled antigen from $^{125}$I-labeled antigen bound by rabbit anti-tag peptide antibody. In a preferred alternative one can measure "on" rates and "off" rates using, for example, a biosensor-based analytical system such as "BIAcore" from Pharmacia Biosensor AB [See, *Nature* 361:186-187 (1993)].

This latter technique requires less antigen than the in vivo immunization because the in vivo method typically requires about 50 micrograms of antigen per mouse per injection and there are usually two boosts following primary immunization for the in vivo method.

For example, antibodies may be raised against an epitope that is unique to NBS-1. For example, the carboxy terminal differs most from p53. In addition, one would use this segment to distinguish the α isoform from the β isoform.

One approach is to isolate a peptide sequence that contains an antigenic determinant for use as an immunogen, such as the C-terminus. This peptide immunogen can be attached to a carrier to enhance the immunogenic response. Although the peptide immunogen can correspond to any portion of a polypeptide encoded by a eukaryotic nucleotide sequence of the invention, certain amino acid sequences are more likely than others to provoke an immediate response, for example, an amino acid sequence including the C-terminus of a polypeptide encoded by a gene that contains nucleotide sequences of the invention. Preferably one can prepare a cell line expressing only the C-terminus, select those cells with the highest levels of expression.

For example, a cDNA clone encoding a NBS-1 or a fragment thereof such as the fragment between the 5' Bam H1 site (1138) and the 3' Mun1 site (1905) may be expressed in a host using standard techniques (see above; see Sambrook et al., Molecular Cloning; A Laboratory Manual, Cold Spring Harbor Press, Cold Spring Harbor, N.Y.: 1989) such that 5-20% of the total protein that can be recovered from the host is the desired protein. Recovered proteins can be electrophoresed using PAGE and the appropriate protein band can be cut out of the gel. The desired protein sample can then be eluted from the gel slice and prepared for immunization. Alternatively, a protein of interest can be purified by using conventional methods such as, for example, ion exchange hydrophobic, size exclusion, or affinity chromatography.

Once the protein immunogen is prepared, mice can be immunized twice intraperitoneally with approximately 50 micrograms of protein immunogen per mouse. Sera from such immunized mice can be tested for antibody activity by immunohistology or immunocytology on any host system expressing such polypeptide and by ELISA with the expressed polypeptide. For immunohistology, active antibodies of the present invention can be identified using a biotin-conjugated anti-mouse immunoglobulin followed by avidin-peroxidase and a chromogenic peroxidase substrate. Preparations of such reagents are commercially available; for example, from Zymad Corp., San Francisco, Calif. Mice whose sera contain detectable active antibodies according to the invention can be sacrificed three days later and their spleens removed for fusion and hybridoma production. Positive supernatants of such hybridomas can be identified using the assays described above and by, for example, Western blot analysis.

To further improve the likelihood of producing an antibody as provided by the invention, the amino acid sequence of polypeptides encoded by a eukaryotic nucleotide sequence of the present invention may be analyzed in order to identify portions of amino acid sequence which may be associated with increased immunogenicity. For example, polypeptide sequences may be subjected to computer analysis to identify potentially immunogenic surface epitopes. Such computer analysis can include generating plots of antigenic index, hydrophilicity, structural features such as amphophilic helices or amphophilic sheets and the like.

The monoclonal antibodies may be human monoclonal antibodies or chimeric human-mouse (or other species) monoclonal antibodies. The present invention provides for antibody molecules as well as fragments of such antibody molecules.

Those of ordinary skill in the art will recognize that a large variety of possible moieties can be coupled to the resultant antibodies or to other molecules of the invention. See, for example, "Conjugate Vaccines", Contributions to Microbiology and Immunology, J. M. Cruse and R. E. Lewis, Jr (eds), Carger Press, New York, (1989), the entire contents of which are incorporated herein by reference.

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, diisocyanates, glutaraldehydes, diazobenzenes and hexamethylene diamines. This listing is not intended to be exhaustive of the various classes of coupling agents known in the art but, rather, is exemplary of the more common coupling agents. (See Killen and Lindstrom 1984, "Specific killing of lymphocytes that cause experimental Autoimmune Myesthenia Gravis by toxin-acetylcholine receptor conjugates." Jour. Immun. 133:1335-2549; Jansen, F. K., H. E. Blythman, D. Carriere, P. Casella, O. Gros, P. Gros, J. C. Laurent, F. Paolucci, B. Pau, P. Poncelet, G. Richer, H. Vidal, and G. A. Voisin. 1982. "Immunotoxins: Hybrid molecules combining high specificity and potent cytotoxicity". Immunological Reviews 62:185-216; and Vitetta et al., supra).

Preferred linkers are described in the literature. See, for example, Ramakrishnan, S. et al., Cancer Res. 44:201-208 (1984) describing use of MBS (M-maleimidobenzoyl-N-hydroxysuccinimide ester). See also, Umemoto et al. U.S. Pat. No. 5,030,719, describing use of halogenated acetyl hydrazide derivative coupled to an antibody by way of an oligopeptide linker. Particularly preferred linkers include: (i) EDC (1-ethyl-3-(3-dimethylamino-propyl) carbodiimide hydrochloride; (ii) SMPT (4-succinimidyloxycarbonyl-alpha-methyl-alpha-(2-pyridyl-dithio)-toluene (Pierce Chem. Co., Cat. (21558G); (iii) SPDP (succinimidyl-6 [3-(2-pyridyldithio) propionamido] hexanoate (Pierce Chem. Co., Cat #21651G); (iv) Sulfo-LC-SPDP (sulfosuccinimidyl 6 [3-(2-pyridyldithio)-propianamide] hexanoate (Pierce Chem. Co. Cat. #2165-G); and (v) sulfo-NHS (N-hydroxysulfo-succinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodiimide couplings. Carbodiimide couplings (such as EDC) when used in conjunction with sulfo-NHS, forms esters that are more resistant to hydrolysis than the carbodiimide coupling reaction alone.

Antibodies of the present invention can be detected by appropriate assays, e.g., conventional types of immunoassays. For example, a sandwich assay can be performed in which the NBS-1 or fragment thereof is affixed to a solid phase. Incubation is maintained for a sufficient period of time to allow the antibody in the sample to bind to the immobilized polypeptide on the solid phase. After this first incubation, the solid phase is separated from the sample. The solid phase is washed to remove unbound materials and interfering substances such as non-specific proteins which may also be present in the sample. The solid phase containing the antibody of interest bound to the immobilized polypeptide of the present invention is subsequently incubated with labeled antibody or antibody bound to a coupling agent such as biotin or avidin. Labels for antibodies are well-known in the art and include radionucleides, enzymes (e.g. maleate dehydrogenase, horseradish peroxidase, glucose oxidase, catalase), fluors (fluorescein isothiocyanate, rhodamine, phycocyanin, fluorescamine), biotin, and the like. The labeled antibodies are incubated with the solid and the label bound to the solid phase is measured, the amount of the label detected serving as a measure of the amount of antibody present in the sample. These and other immunoassays can be easily performed by those of ordinary skill in the art.

These antibodies can be used to select target cells where a specific NBS-1 function is desired. Preferably one chooses a target cell where NBS-1 expression is dormant or low. More preferably, it is dormant. The NBS-1 gene or fragment thereof can be introduced into a target cell by any method which will result in the uptake and expression of the NBS-1 gene by the target cells. These can include vectors, liposomes, naked DNA, adjuvant-assisted DNA, catheters, etc. Vectors include chemical conjugates such as described in WO 93/04701, which has targeting moiety (e.g. a ligand to a cellular surface receptor), and a nucleic acid binding moiety (e.g. polylysine), viral vector (e.g. a DNA or RNA viral vector), fusion proteins such as described in PCT/US 95/02140 (WO 95/22618) which is a fusion protein containing a target moiety (e.g. an antibody specific for a target cell) and a nucleic acid binding moiety (e.g. a protamine), plasmids, phage, etc. The vectors can be chromosomal, nonchromosomal or synthetic.

Preferred vectors include viral vectors, fusion proteins and chemical conjugates. Retroviral vectors include moloney murine leukemia viruses and HIV-based viruses. One preferred HIV-based viral vector comprises at least two vectors wherein the gag and pol genes are from an HIV genome and the env gene is from another virus. DNA viral vectors are preferred. These vectors include pox vectors such as orthopox or avipox vectors, herpesvirus vectors such as a herpes simplex I virus (HSV) vector [Geller, A. I. et al., *J. Neurochem,* 64:487 (1995); Lim, F., et al., in DNA Cloning: *Mammalian Systems, D. Glover, Ed. (Oxford Univ. Press, Oxford England)* (1995); Geller, A. I. et al., *Proc Natl. Acad. Sci.*: U.S.A.:90 7603 (1993); Geller, A. I., et al., *Proc Natl. Acad. Sci USA:* 87:1149 (1990)], Adenovirus Vectors [LeGal LaSalle et al., *Science,* 259:988 (1993); Davidson, et al., *Nat. Genet* 3:219 (1993); Yang, et al., *J. Virol.* 69: 2004 (1995)] and Adeno-associated Virus Vectors [Kaplitt, M. G., et al., *Nat. Genet.* 8:148 (1994)].

Pox viral vectors introduce the gene into the cells cytoplasm. Avipox virus vectors result in only a short term expression of the NBS-1 gene. Adenovirus vectors, adeno-associated virus vectors and herpes simplex virus (HSV) vectors are preferred for introducing the NBS-1 gene into neural cells. The adenovirus vector results in a shorter term expression (about 2 months) than adeno-associated virus (about 4 months), which in turn is shorter than HSV vectors. The particular vector chosen will depend upon the target cell and the condition being treated. The introduction can be by standard techniques, e.g. infection, transfection, transduction or transformation. Examples of modes of gene transfer include naked DNA, $CaPO_4$ precipitation, DEAE dextran, electroporation, protoplast fusion, lipofecton, cell microinjection, viral vectors, etc.

For example, one can use the vector to target any desired target cell such as a glioma. For example, stereotaxic injection can be used to direct the vectors (e.g. adenovirus, HSV) to a desired location in the brain (e.g. a glioma). Stereotaxic surgery is performed using standard neurosurgical procedures (Pellegrino and Cushman, (1971)). Additionally, the particles can be delivered by intracerebroventricular ("icv") infusion using a minipump infusion system, such as a SynchroMed Infusion System. A method based on bulk flow, termed convection, has also proven effective at delivering large molecules to extended areas of the brain and may be useful in delivering the vector to the target cell (Bobo et al., *Proc. Natl. Acad. Sci. USA* 91:2076-2080 (1994); Morrison et al., *Am. J. Physiol.* 266:292-305 (1994)). Other methods that can be used including catheters, or parenteral (including intraperitoneal, subcutaneous injection, intravenous, intranasal, intramuscular or infusion techniques), oral or other known routes of administration.

One would inject a sufficient amount of the vector to obtain a serum concentration in the NSB-1 target cell ranging between about 1 pg/ml to 20 μg/ml. More preferably between 0.1 μg/ml to 10 μg/ml. Still more preferably, between about 0.5 μg/ml to 10 μg/ml.

In addition to the antibodies and NBS-1 one can also use other compounds to obtain a specific effect. Such compositions may be employed alone or in combination with acceptable carriers such as those described below. Suitable effective dose of the desired active compound in a composition will be in the range of 1 to 10,000 μg per kilogram body weight of recipient per day, preferably in the range of 10 to 4,000 μg per kilogram body weight of recipient per day.

Kits containing the antibody, vector or other NBS-1 molecule can be prepared. Preferably, the molecule is in a container. One preferred kit would be a probe for NBS-1 levels such as an NBS-1 antibody. This probe can be used to select subjects having p53-dependent malignant cells that are susceptible to treatment by enhancing NBS-1 levels. Preferably, the kit contains instructions for the use of the molecule, e.g., how to use the NBS-1 probe to select subjects.

The molecule may be administered alone, or as part of a pharmaceutical composition, comprising at least one active compound together with one or more acceptable carriers thereof and optionally other therapeutic ingredients. The carrier(s) must be "acceptable" in the sense of being compatible with the other ingredients of the formulation and not deleterious to the recipient thereof.

The compositions include those suitable for oral, rectal, nasal, topical (including buccal and sublingual), vaginal or parenteral (including subcutaneous, intramuscular, intravenous and intradermal) administration. The formulations may conveniently be presented in unit dosage form, e.g., tablets and sustained release capsules, and in liposomes, and may be prepared by any methods well know in the art of pharmacy.

Such methods include the step of bringing into association with the molecule to be administered ingredients such as the carrier which constitutes one or more accessory ingredients. In general, the compositions are prepared by uniformly and intimately bringing into association the active ingredients with liquid carriers, liposomes or finely divided solid carriers or both, and then if necessary shaping the product.

Compositions of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion, or packed in liposomes and as a bolus, etc.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

Compositions suitable for topical administration include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Compositions suitable for a topical administration to the skin may be presented as ointments, creams, gels and pastes comprising one or more compounds of the present invention and a pharmaceutically acceptable carrier. A suitable topical delivery system is a transdermal patch containing the ingredient to be administered.

Compositions suitable for rectal administration may be presented as a suppository with a suitable base comprising, for example, cocoa butter or a salicylate.

Compositions suitable for nasal administration wherein the carrier is a solid include a coarse powder having a particle size, for example, in the range 20 to 500 microns which is administered in the manner in which a compound is inhaled i.e., by rapid inhalation through the nasal passage from a container of the powder held close up to the nose. Suitable formulations wherein the carrier is a liquid, for administration, as for example, a nasal spray or as nasal drops, include aqueous or oily solutions of the active ingredient.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets of the kind previously described.

It should be understood that in addition to the ingredients particularly mentioned above the formulations of this invention may include other agents conventional in the art having regard to the type of formulation in question, for example, those suitable for oral administration may include flavoring agents.

For example, solid dose forms that can be used for oral administration include capsules, tablets, pills, powders and granules. In such solid dose forms, the active ingredient, i.e., the NSB-1 gene and/or other molecule is mixed with at least one insert carrier such as sucrose, lactose or starch. Such dose forms can also comprise additional substances other than inert diluents, e.g., lubricating agents, such as magnesium stearate. Furthermore, the dose forms in the case of capsules, tablets and pills may also comprise buffering agents. The tablets, capsules and pills can also contain time-release coatings to release the particles over a predetermined time period.

For parenteral administration, one typically includes sterile aqueous or non-aqueous solutions, suspensions or emulsions in association with a pharmaceutically acceptable parenteral vehicle. Examples of non-aqueous solvents or vehicles are propylene glycol, polyethylene glycol, vegetable oils such as olive oil and corn oil, gelatin and injectable organic esters, such as ethyl oleate. These dose forms may also contain adjuvants such as preserving, wetting, emulsifying and dispersing agents. They may be sterilized by, for example, filtration through a bacterial-retaining filter, by incorporating sterilizing agents into the composition, by irradiating the compositions, etc., so long as care is taken not to inactivate the active ingredient (e.g. a vector). They can also be manufactured in a medium of sterile water or some other sterile injectable medium before use. Further examples of these vehicles include saline, Ringer's solution, dextrose solution and 5% human serum albumin. Liposomes may also be used as carriers. Additives, such as substances that enhance isotonicity and chemical stability, e.g., buffers and preservatives, may also be used.

An exemplary pharmaceutical composition is a therapeutically effective amount of a NBS-1 functional domain, a prodrug that activates NBS-1 expression, an antibody etc., optionally included in a pharmaceutically-acceptable and compatible carrier. The term "pharmaceutically-acceptable and compatible carrier" as used herein, and described more fully below, includes (i) one or more compatible solid or liquid filler diluents or encapsulating substances that are suitable for administration to a human or other animal, and/or (ii) a system, such as a DNA or retroviral vector, capable of delivering the molecule to a target cell. In the present invention, the term "carrier" thus denotes an organic or inorganic ingredient, natural or synthetic, with which the molecules of the invention are combined to facilitate application. The term "therapeutically-effective amount" is that amount of the present pharmaceutical compositions which produces a desired result or exerts a desired influence on the particular condition being treated. Various concentrations may be used in preparing compositions incorporating the same ingredient to provide for variations in the age of the patient to be treated, the severity of the condition, the duration of the treatment and the mode of administration.

The term "compatible", as used herein, means that the components of the pharmaceutical compositions are capable of being commingled with a small molecule, nucleic acid and/or polypeptides of the present invention, and with each other, in a manner such that does not substantially impair the desired pharmaceutical efficacy.

Dose of the pharmaceutical compositions of the invention will vary depending on the subject and upon particular route of administration used. Dosages can range from those resulting in a serum concentration of about 1 pg/ml to about 300 µg per day, more preferably about 1 to 10,000 µg/kg. By way of an example only, an overall dose range of from about, for example, 1 microgram to about 300 micrograms per kg might be used for human use. This dose can be delivered at periodic intervals based upon the composition and its purpose. For example, where the composition is intended to promote NBS-1 expression by a vector encoding NBS-1 periodic administration based upon level of expression. Other compounds such as a prodrug enhancing NBS-1 expression might be administered daily. Pharmaceutical compositions of the present invention can also be administered to a subject according to a variety of other, well-characterized protocols. Desired time intervals for delivery of multiple doses of a particular composition can be determined by one of ordinary skill in the art employing no more than routine experimentation.

The small molecules and polypeptides of the invention may also be administered per se (neat) or in the form of a pharmaceutically acceptable salt. When used in medicine, the salts should be pharmaceutically acceptable, but non-pharmaceutically acceptable salts may conveniently be used to prepare pharmaceutically acceptable salts thereof and are not excluded from the scope of this invention.

Pharmaceutically acceptable salts include, but are not limited to, those prepared from the following acids: hydrochloric, hydrobromic, sulfuric, nitric, phosphoric, maleic, acetic, salicylic, p-toluene-sulfonic, tartaric, citric, methanesulphonic, formic, malonic, succinic, naphthalene-2-sulfonic, and benzenesulphonic. Also, pharmaceutically acceptable salts can be prepared as alkaline metal or alkaline earth salts, such as sodium, potassium or calcium salts of the carboxylic acid group. Thus, the present invention also provides pharmaceutical compositions, for medical use, which comprise nucleic acid and/or polypeptides of the invention together with one or more pharmaceutically acceptable carriers thereof and optionally any other therapeutic ingredients.

Preferred compositions suitable for parenteral administration conveniently comprise a sterile aqueous preparation of the molecule of the invention which is preferably isotonic with the blood of the recipient. This aqueous preparation may be formulated according to known methods using those suitable dispersing or wetting agents and suspending agents. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectibles.

EXAMPLES

The following Examples serve to illustrate the present invention, and are not intended to limit the invention in any manner.

Methods: NBS-1 cDNAs were ligated as XhoI/XbaI fragments into a pCMV1 vector containing a 200-bp lamin 5' untranslated region and encoding an N-terminal HA tag (Heald R, et al., *Cell* 74:463-74 (1993)). The cDNAs were then excised as BglII-XbaI fragments and subcloned into pCDNA3(Invitrogen). See FIGS. 2A-C. SAOS2 Cells were transfected using the BBS-CaPO method of Chen C & Okayama H. *Molecular and Cellular Biology* 7:2745-2752 (1987)) and lysed 48 hours later in EBC buffer (50 mM Tris[pH 8.0], 120 mM NaCl, 0.5% NP-40) supplemented with aprotonin (11.5 µg/ml), leupeptin (5 µg/ml), phenylmethyl sulfonyl fluoride (50 µg/ml), 100 mM NaF, 0.2 mM $Na_3VO_4$). 150 µg aliquots of cell extract, as determined by the Bradford Method, were resolved by electrophoresis in a 10% SDS-polyacrylamide gel, transferred to a nylon membrane, and probed with anti-HA antibody (12CA5; Boehringer-Mannheim). Bound protein was detected colorimetrically using an alkaline phosphatase conjugated goat anti-mouse antibody (Fisher). Anti-HA (12CA5) immunoprecipitates recovered on protein A sepharose and eluted by boiling in SDS-containing sample buffer were similarly analyzed. See FIGS. 2A-C. BHK cells were grown on coverslips and transfected using the calcium phosphate method (Graham F L & van der Eb A. *J Viron* 52:456-467)). 12 hours following the removal of the DNA precipitates the cells were processed from immunofluorescence essentially as described previously (Heald R, et al., *Cell* 74:463-74 (1993)). The primary antibody used was anti-HA antibody (12CA5 hybridoma supernatant diluted 1:50), and the secondary was FITC-conjugated anti-mouse antibody (diluted 1:500; Boehringer-Mannheim).

2XRGC-CAT and β-Globin-CAT were a gift of Dr. Erik Flemington. 2XRGC-CAT was generated by introducing double stranded oligonucleotides containing two RGC p53 sites (Chen X, et al., *Genet Dev* 7:1837-1849 (1993)) upstream from the β-globin minimal promoter in β-globin-CAT (Flemington E K, et al., *Mol Cell Biol* 14:3041-3052 (1994)). The p21 reporter plasmids were a generous gift of Drs. Dalia Cohen and Ker Yu (Sandoz Research Institute, East Hanover N.J.). An ~5.5 kB BamH1-BamH1 p21 clone was isolated from a human placental genomic library (Clontech) using a PCR generated 188 bp probe spanning the p21 transcriptional initiation site and subcloned into pBSK+ (Stratagene). The 3' end of this p21 clone was digested with ExoIII nuclease followed by ligation to an XhoI linker such that it corresponded to −4.7 kB to +51 bp with respect to the transcriptional initiation site (el-Deiry W S, et al., *Cell* 75:817-925 (1993)). A 2.7 kB EcoR1-XhoI (−2.7 kb −+51 bp) fragment was subcloned into pGL2-basic to generate p21-wt luc. This plasmid was restricted with KpnI and MluI and digested with ExoIII nuclease to generate a nested set of 5' deletion mutants. p21 del 8 contains −514 −+51 bp, includes two SP1 sites and the p21 TATA box (el-Deiry W S, et al., *Cancer Res* 55:2910-2919 (1995); el-Deiry W S, et al., *Cell* 75:817-925 (1993)), but lacks the two p53 binding sites present in p21 wt luc. pCMV-p53 and pCMV-p53V143A were gifts of Dr. Bert Vogelstein (Baker S J, et al., *Science* 249:912-915 (1990)). Cells were transfected using the BBS-CaPO4 method with 5 µg of the indicated reporter plasmid, 2 µg of pCMV-βgal, 1-2 µg of the indicated expression plasmids, and pRcCMV (Invitrogen) as a carrier plasmid to a total of 20 µg. Luciferase, β-galactosidase, and CAT assays were performed as described previously 24 hours following the removal of the DNA precipitates (Flemington E K, et al., *Mol Cell Biol* 14:3041-3052(1994); Krek W, et al., *Science* 262:1557-1560 (1993)). See FIGS. 3A and 3B.

SAOS2 cells were transfected by the BBS method with 20 µg of the indicated expression plasmids. 48 hours later the cells were placed under G418 selection (600 µg/ml). The cells were fixed and stained with crystal violet, as described previously (Baker S J, et al., *Science* 249:912-915 (1990); Qin XQ, et al., *Genet Dev* 6:953-964 (1992)), approximately 2 weeks later and photographed (FIGS. 4A-4E).

SAOS2 cells were transfected with 20 μg of the indicated expression plasmids along with 2 μg of a plasmid encoding the cell surface marker CD19 (pCD19; a gift of Dr. Thomas Tedder). Anti-CD19 antibody B4 was provided by Dr. John Gribben. Analysis of CD19 positive cells for DNA content by FACS was performed approximately 72 hours later as described previously (Seller W R, et al., *Proc Natl Acad Sci USA* 92:11544-11548 (1995)).

BHK cells were transfected by the BBS method with 20 μg of either p53 or NSB-1α expression plasmid. Following the removal of the DNA precipitate, the cells were placed in serum-free media. 16 hours later, the cells were fixed in PBS+4% formaldehyde, washed twice with PBS, and permeabilized in 70% ethanol (prechilled to −20° C.) for 30 minutes at room temperature. Following two washes with PBS, TUNEL staining was performed essentially as described previously, except that FITC-dUTP(Boehringer-Mannheim) was used in place of biotinylated dUTP (Gavrieli Y, et al., *J. Cell Biol.* 119:493-501 (1992)). The cells were then processed for immunofluorescence using the anti-p53 antibody 1801 (diluted 1:500; Oncogene Science), or the anti-HA antibody, as described above. The secondary antibody used was rhodamine-conjugated anti-mouse (diluted 1:500; Boehringer-Mannheim) (FIGS. 4F-4K).

Monoclonal antibodies were prepared by using the carboxy terminal of NSB-1. We took the region between the 5' Bam H1 site (1138) and the 3' Mun1 site (1905). The 5' primer was CGC GGA TCC TTG GTG CCG CAG CCG CTG GTA GAC (SEQ ID NO:26). The 3' primer was TAG CCA ATT GTC AGT GGA TCT CGG CCT CCG TGA A (SEQ ID NO:27). This cDNA was then subjected to PCR and inserted into the pGex2T plasmid at the Bam H1 and EcoR1 sites. This resulted in the GST fusions GST NBS-1α encoding amino acids 380-637 ("ER") and GST NSB-1β encoding amino acids 380-500 ("GC"). See FIG. 10A. These GST fusions were injected into mice. Thereafter using standard techniques antibodies were obtained and hybridomas prepared.

Hybridoma supernatants were screened by ELISA using 96 well plates coated with the GST-NBS1 protein used for immunization. Binding was detected using an alkaline phosphatase conjugated anti-mouse antibody.

Supernatants which scored positively by ELISA were then screened for their ability to immunoprecipitate 35S-labelled NBS1 in vitro translate (using NBS1 cDNAs and TNT reticulocyte lysate from Promega) and for their ability to react with GST-NBS1 by western blot analysis. For the latter, crude bacterial extracts containing the GST-NBS1 immunogen were loaded in preparative wells, resolved by SDS-polyacrylamide gel electrophoresis, and transferred to nitrocellulose. The nitrocellulose filters were then placed in a multiwell press to facilitate probin with multiple independent supernatants.

The positive supernatants were not systematically assayed against p53 because the fragments of NBS1 used as immunogens were chosen based on their complete lack of similarity with p53. We have not seen any evidence of cross reactivity of our antibodies with p53.

Mammalian expression plasmids were made in which NBS-1 cDNAs for two naturally occurring NBS-1 isoforms were placed under the control of a cytomegalovirus promoter. These two isoforms, designated NBS-1α and NBS-1β, differ in their C-termini as a result of differential spicing of the NSB-1 mRNA. Both isoforms contain the residues which, based on the p53 structure, are likely to participate in DNA recognition. In addition, site-directed mutagenesis was used to make plasmids encoding the two NBS-1 isoforms in which one of the these residues (Arg 292) was changed to Histidine. The corresponding p53 mutant (Arg 273 His) does not bind to canonical p53 DNA binding sites and is defective for transcriptional activation and tumor suppression functions (Kern S E, et al., *Science* 256:827-829 (1992)). All of these plasmids introduced an N-terminal hemagglutinin epitope tag to facilitate the identification of its protein product and also contained a neomycin resistance marker.

Figure 2A:
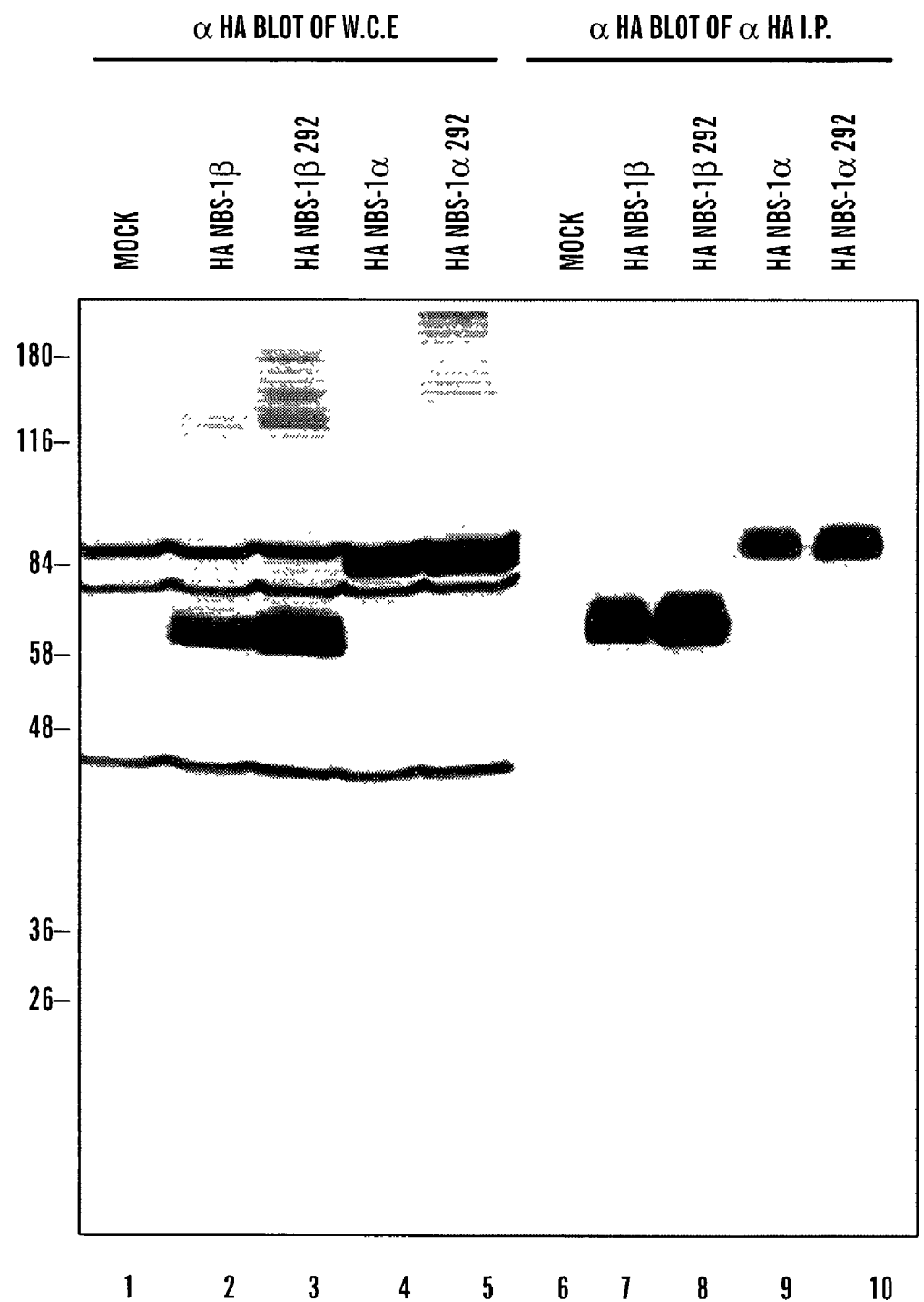
Figure 2F:
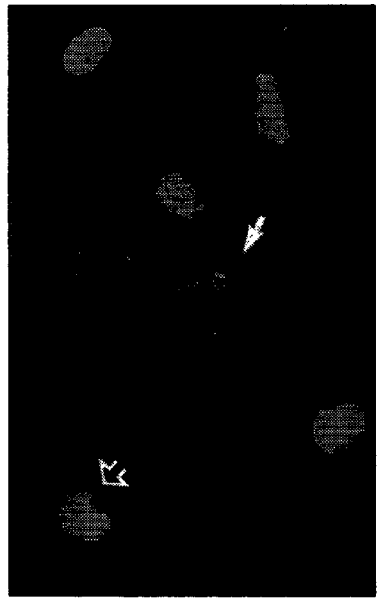
Figure 2H:
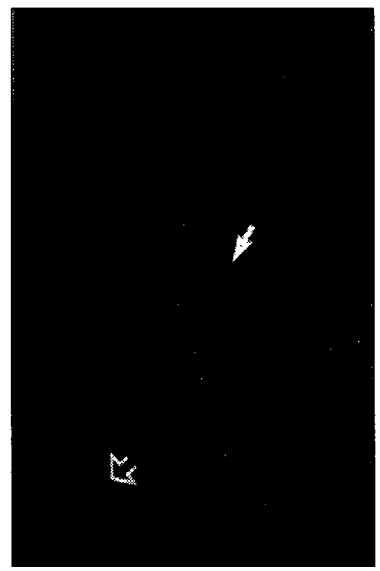
Figure 2G:
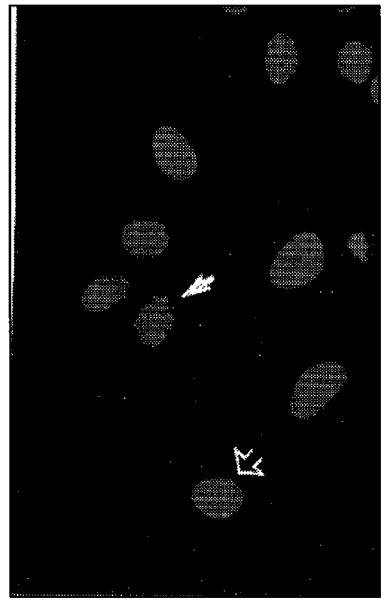
Figure 2I:
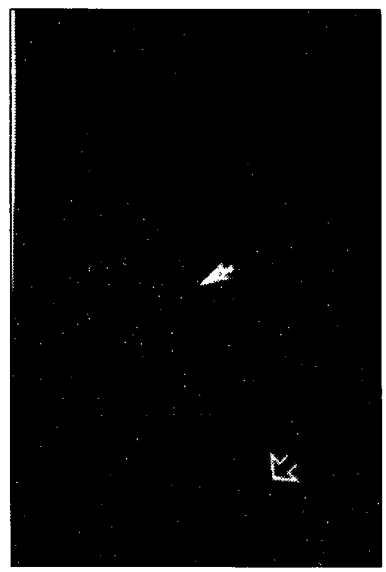

Each plasmid gave rise to a comparably stable protein of the expected size as determined by anti-HA steady state western blot analysis of transiently transfected cells (FIG. 2A). Furthermore, each of the exogenous NSB-1 species appeared to be nuclear based on anti-HA immunofluorescence staining (FIG. 2B and 2C).

Figure 3A:
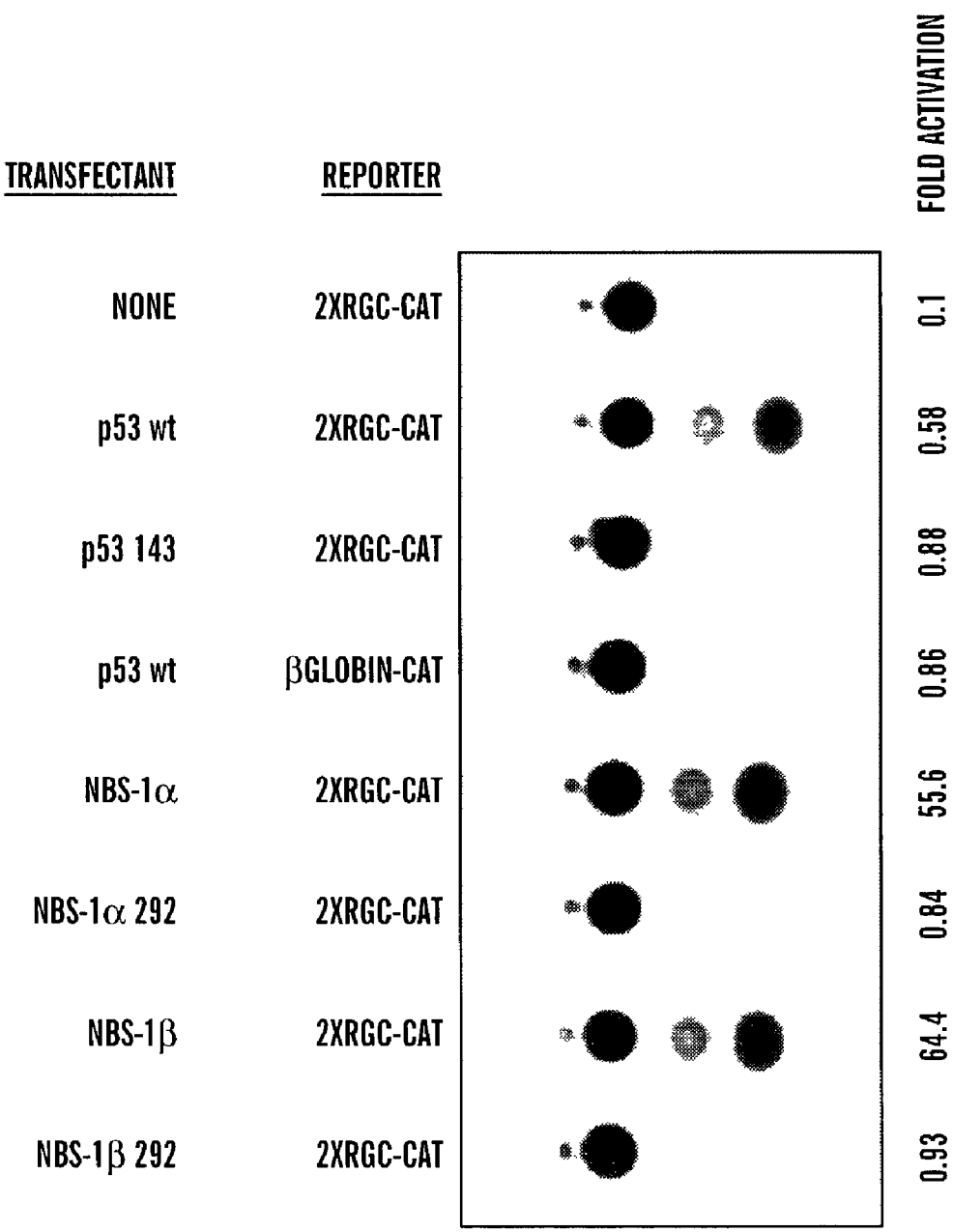
FIGS. 3A and 3B show NBS-1 activates p53 responsive promoters.
Figure 3B:
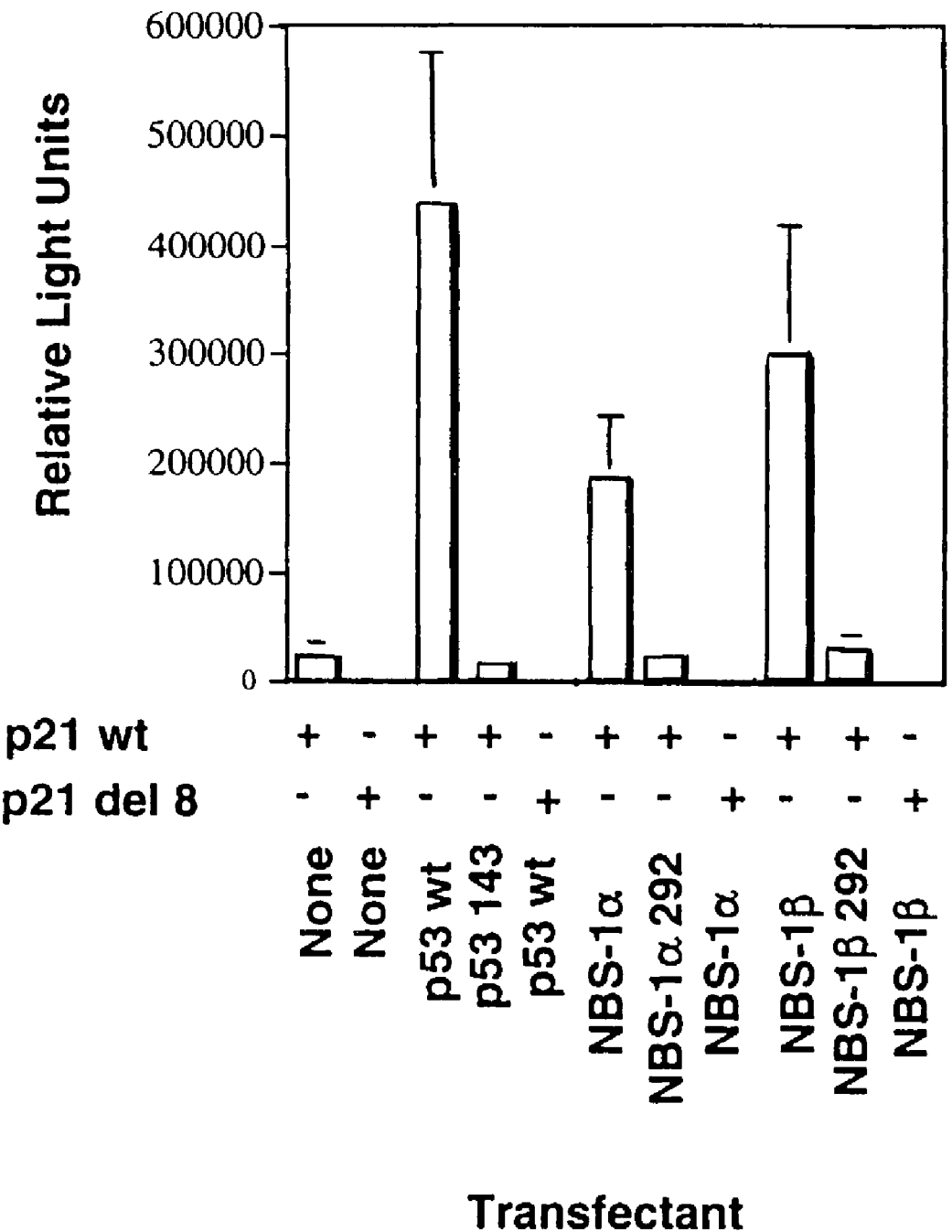
Figure 4A:
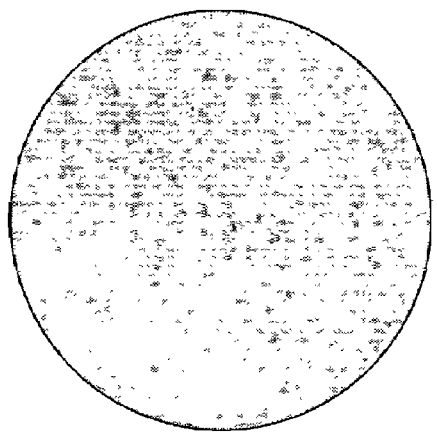
FIGS. 4A-4K show NBS-1 suppresses tumor cell growth and induces apoptosis.
Figure 4B:
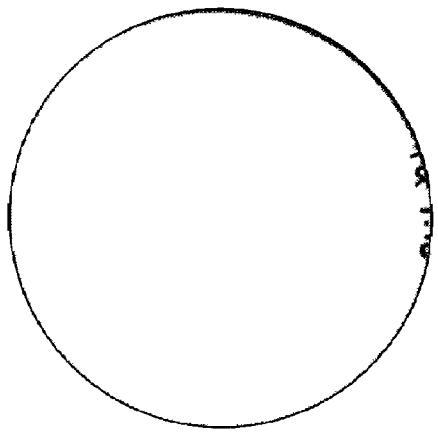
Figure 4D:
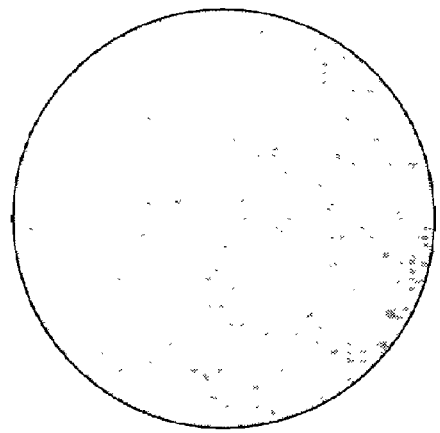
Figure 4C:
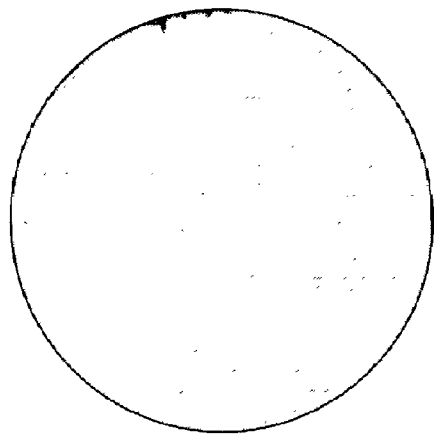
Figure 4E:
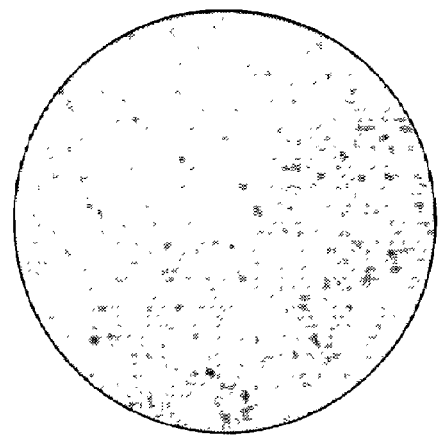
Figure 4F:
Figure 4I:
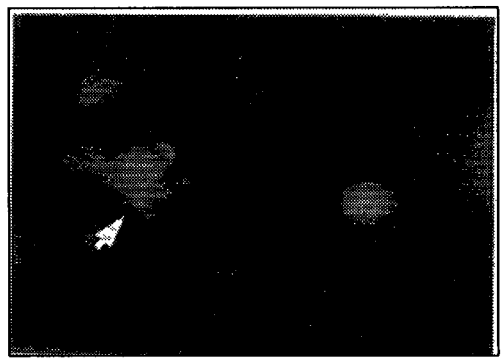
Figure 4G:
Figure 4J:
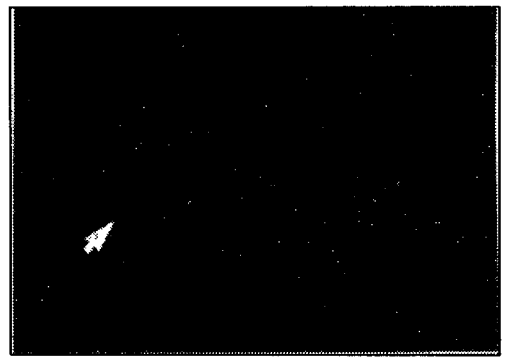
Figure 4H:
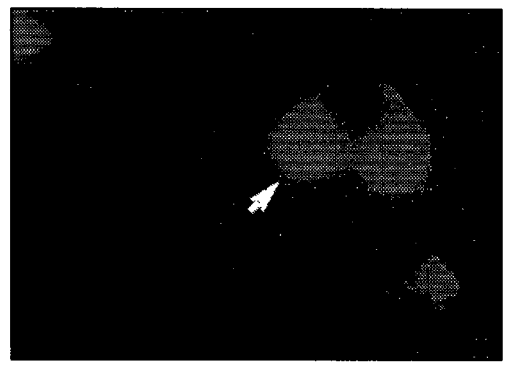
Figure 4K:
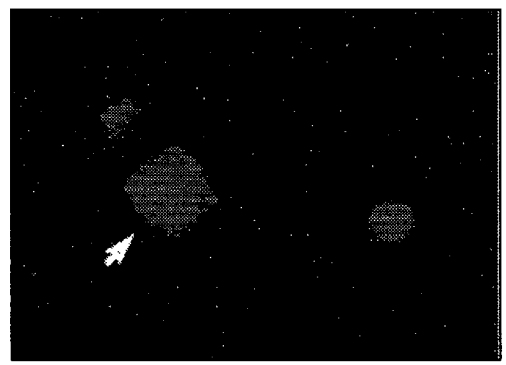

SAOS2 cells, which lack functional p53 (Diller L, et al., *Mol. Cell. Biol.* 10:5772-5781 (1990)), were transfected with a CAT reporter plasmid containing a minimal promoter consisting of two p53 binding sites upstream of a TATA box (2XRGC-CAT). Cotransfection of a plasmid encoding wild-type p53 led to measurable CAT activity, whereas a tumor derived p53 mutant (143Ala), did not (FIG. 3A). Likewise, cotransfection with either of the two wild-type NBS-1 expression plasmids led to high levels of CAT activity, whereas the NBS-1 292His derivatives did not. None of the expression plasmids activated a CAT reporter containing the β-globin promoter (FIG. 3A and data not shown). Similarly, wild-type p53, as well as the two wild-type NBS-1 isoforms, were capable of activating transcription from a reporter plasmid in which the p21 promoter was placed upstream of a luciferase cDNA (p21 wt) (el-Deiry W S, et al., *Cancer Res* 55:2910-2919 (1995))(FIG. 3B). Neither the p53 143Ala nor the NBS-1 292His mutants were able to activate transcription from the p21 wt reporter. Furthermore, a p21 promoter mutant lacking functional p53 binding sites (p21 de18) was unaffected by either p53 or NBS-1. Thus, these experiments suggest that NBS-1 can activate transcription from promoters containing p53 DNA binding sites.

Reintroduction of wild-type p53 suppresses the growth of SAOS2 cells (Diller L, et al., *Mol. Cell. Biol.* 10:5772-5781 (1990)). To determine whether NBS-1 might likewise have this effect, SAOS2 cells were transfected with the NBS-1 expression plasmids and were placed under G418 selection. Approximately two weeks later, drug resistant colonies were stained with crystal violet and photographed. Transfection with either of the two wild-type NBS-1 expression plasmids gave rise to virtually no macroscopic colonies (FIGS. 4A-4E), in keeping with earlier results with wild-type p53. In contrast, many drug resistant colonies formed following transfection with the backbone expression plasmid (pcDNA-3) or with the plasmids encoding the NBS-1 mutants.

The suppression of SAOS2 cell growth by p53 is thought to be due largely to apoptosis (Pietenpol J A, et al., *Proc. Natl. Acad. Sci.* 91:1998-2002 (1994)). SAOS2 cells were transiently transfected with a plasmid encoding the cell surface marker CD19 along with plasmids encoding either p53 or NSB-1. The DNA content of CD19 positive cells was then analyzed by fluorescence activated cell sorting (FACS). Wild-type, but not mutant, p53 led to a significant increase in the number of cells undergoing apoptosis (cells with less than 2N DNA content) compared with cells transfected with the backbone expression plasmid. Similar effects were observed with the two wild-type NBS-1 species, whereas the corresponding NBS-1 mutants were virtually inert.

Due to the relatively high basal levels of apoptosis in SAOS2 cells, we next transiently transfected Baby Hamster Kidney (BHK) cells with these expression plasmids. Wild-type p53, as well as each of the two wild-type NBS-1 species, induced apoptosis in these cells as determined by changes in nuclear morphology and TUNEL assays performed 36 hours after transfection (FIGS. 4F-4K). In contrast, apoptosis was not observed in cells transfected with the backbone expression plasmid and was greatly diminished when the corresponding p53 and NBS-1 mutants were tested in parallel (data not shown).

These results indicate that NBS-1 can, at least when produced at high levels, activate p53 responsive genes and act as a growth suppressor. The latter appears to be due, at least in part, to the induction of apoptosis. Thus, NBS-1 appears to be both a structural and functional homolog of p53. It is perhaps noteworthy that p53 mutations are exceedingly rare in neuroblastomas (Hosoi G., et al., *Cancer* 73:3087-93 (1994);

Vogan K, et al., *Cancer Res* 53:5269-73 (1993)). It appears that NSB-1, rather than p53, is the physiologically relevant 'p53-like' protein in the precursor cells which give rise to neuroblastomas, for reasons presently unknown, and that consequently it, rather than p53, is targeted for mutation in these tumors.

All references described herein are incorporated by reference.

The invention has been described in detail with reference to preferred embodiments thereof. However, it will be appreciated that those skilled in the art, upon consideration of this disclosure, may make modifications and improvements within the spirit and scope of the invention.

We claim:

1. A purified antibody that specifically binds to human p73 protein consisting of SEQ ID NO:3, but does not bind to p53 protein consisting of SEQ ID NO:4.

2. The antibody of claim 1, which is selected from the group consisting of polyclonal antibodies, monoclonal antibodies and single chain antibodies.

3. The antibody of claim 1, wherein said antibody is detectably labeled.

4. A kit containing a probe for specifically detecting p73 protein consisting of SEQ ID NO:3, wherein the probe is an antibody that specifically binds to the p73 protein consisting of SEQ ID NO: 3 but does not bind to p53 protein consisting of SEQ ID NO:4.

5. The kit of claim 4, wherein said antibody is present in a sealed ampule or vial.

6. The kit of claim 4, wherein said antibody is stored under lyophilized conditions.

7. The kit of claim 4, further containing a label for the antibody.

8. The kit of claim 4, wherein said detecting comprises measuring a level of said p73 protein consisting of SEQ ID NO:3.

* * * * *

SEQUENCE LISTING

```
<160> NUMBER OF SEQ ID NOS: 27

<210> SEQ ID NO 1
<211> LENGTH: 6
<212> TYPE: PRT
<213> ORGANISM: Homo sapien

<400> SEQUENCE: 1

Thr Phe Ser Asp Leu Trp
1               5

<210> SEQ ID NO 2
<211> LENGTH: 6
<212> TYPE: PRT
<213> ORGANISM: Homo sapiens

<400> SEQUENCE: 2

Thr Phe Glu Asp Leu Trp
1               5

<210> SEQ ID NO 3
<211> LENGTH: 636
<212> TYPE: PRT
<213> ORGANISM: Homo sapiens

<400> SEQUENCE: 3

Met Ala Gln Ser Thr Ala Thr Ser Pro Asp Gly Gly Thr Thr Phe Glu
1               5                   10                  15

His Leu Trp Ser Ser Leu Glu Pro Asp Ser Thr Tyr Phe Asp Leu Pro
                20                  25                  30

Gln Ser Ser Arg Gly Asn Asn Glu Val Val Gly Gly Thr Asp Ser Ser
            35                  40                  45

Met Asp Val Phe His Leu Glu Gly Met Thr Thr Ser Val Met Ala Gln
        50                  55                  60

Phe Asn Leu Leu Ser Ser Thr Met Asp Gln Met Ser Ser Arg Ala Ala
65                  70                  75                  80

Ser Ala Ser Pro Tyr Thr Pro Glu His Ala Ala Ser Val Pro Thr His
                85                  90                  95

Ser Pro Tyr Ala Gln Pro Ser Ser Thr Phe Asp Thr Met Ser Pro Ala
            100                 105                 110

Pro Val Ile Pro Ser Asn Thr Asp Tyr Pro Gly Pro His His Phe Glu
        115                 120                 125

Val Thr Phe Gln Gln Ser Ser Thr Ala Lys Ser Ala Thr Trp Thr Tyr
    130                 135                 140

Ser Pro Leu Leu Lys Lys Leu Tyr Cys Gln Ile Ala Lys Thr Cys Pro
```

```
                145                 150                 155                 160
Ile Gln Ile Lys Val Ser Thr Pro Pro Pro Gly Thr Ala Ile Arg
                165                 170                 175

Ala Met Pro Val Tyr Lys Lys Ala Glu His Val Thr Asp Val Lys
            180                 185                 190

Arg Cys Pro Asn His Glu Leu Gly Arg Asp Phe Asn Glu Gly Gln Ser
        195                 200                 205

Ala Pro Ala Ser His Leu Ile Arg Val Glu Gly Asn Asn Leu Ser Gln
        210                 215                 220

Tyr Val Asp Pro Val Thr Gly Arg Gln Ser Val Val Pro Tyr
225                 230                 235                 240

Glu Pro Pro Gln Val Gly Thr Glu Phe Thr Thr Ile Leu Tyr Asn Phe
                245                 250                 255

Met Cys Asn Ser Ser Cys Val Gly Gly Met Asn Arg Arg Pro Ile Leu
                260                 265                 270

Ile Ile Ile Thr Leu Glu Met Arg Asp Gly Gln Val Leu Gly Arg Arg
                275                 280                 285

Ser Phe Glu Gly Arg Ile Cys Ala Cys Pro Gly Arg Asp Arg Lys Ala
            290                 295                 300

Asp Glu Asp His Tyr Arg Glu Gln Gln Ala Leu Asn Glu Ser Ser Ala
305                 310                 315                 320

Lys Asn Gly Ala Ala Ser Lys Arg Ala Phe Lys Gln Ser Pro Pro Ala
                325                 330                 335

Val Pro Ala Leu Gly Ala Gly Val Lys Lys Arg Arg His Gly Asp Glu
                340                 345                 350

Asp Thr Tyr Tyr Leu Gln Val Arg Gly Arg Glu Asn Phe Glu Ile Leu
                355                 360                 365

Met Lys Leu Lys Glu Ser Leu Glu Leu Met Glu Leu Val Pro Gln Pro
            370                 375                 380

Leu Val Asp Ser Tyr Arg Gln Gln Gln Gln Leu Leu Gln Arg Pro Ser
385                 390                 395                 400

His Leu Gln Pro Pro Ser Tyr Gly Pro Val Leu Ser Pro Met Asn Lys
                405                 410                 415

Val His Gly Gly Met Asn Lys Leu Pro Ser Val Asn Gln Leu Val Gly
                420                 425                 430

Gln Pro Pro Pro His Ser Ser Ala Ala Thr Pro Asn Leu Gly Pro Val
            435                 440                 445

Gly Pro Gly Met Leu Asn Asn His Gly His Ala Val Pro Ala Asn Gly
            450                 455                 460

Glu Met Ser Ser Ser His Ser Ala Gln Ser Met Val Ser Gly Ser His
465                 470                 475                 480

Cys Thr Pro Pro Pro Tyr His Ala Asp Pro Ser Leu Val Ser Phe
                485                 490                 495

Leu Thr Gly Leu Gly Cys Pro Asn Cys Ile Glu Tyr Phe Thr Ser Gln
            500                 505                 510

Gly Leu Gln Ser Ile Tyr His Leu Gln Asn Leu Thr Ile Glu Asp Leu
            515                 520                 525

Gly Ala Leu Lys Ile Pro Glu Gln Tyr Arg Met Thr Ile Trp Arg Gly
            530                 535                 540

Leu Gln Asp Leu Lys Gln Gly His Asp Tyr Ser Thr Ala Gln Gln Leu
545                 550                 555                 560

Leu Arg Ser Ser Asn Ala Ala Thr Ile Ser Ile Gly Gly Ser Gly Glu
                565                 570                 575
```

```
Leu Gln Arg Gln Arg Val Met Glu Ala Val His Phe Arg Val Arg His
            580                 585                 590

Thr Ile Thr Ile Pro Asn Arg Gly Gly Pro Gly Gly Gly Pro Asp Glu
            595                 600                 605

Trp Ala Asp Phe Gly Phe Asp Leu Pro Asp Cys Lys Ala Arg Lys Gln
610                 615                 620

Pro Ile Lys Glu Glu Phe Thr Glu Ala Glu Ile His
625                 630                 635

<210> SEQ ID NO 4
<211> LENGTH: 394
<212> TYPE: PRT
<213> ORGANISM: Homo sapiens

<400> SEQUENCE: 4

Met Glu Glu Pro Gln Ser Asp Pro Ser Val Glu Pro Pro Leu Ser Gln
 1               5                  10                  15

Glu Thr Phe Ser Asp Leu Trp Lys Leu Leu Pro Glu Asn Asn Val Leu
                20                  25                  30

Ser Pro Leu Pro Ser Gln Ala Met Asp Asp Leu Met Leu Ser Pro Asp
            35                  40                  45

Asp Ile Glu Gln Trp Phe Thr Glu Asp Pro Gly Pro Asp Glu Ala Pro
        50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gly Ser Tyr Gly Gly Tyr Gly Phe Arg
            100                 105                 110

Leu Gly Phe Leu His Ser Gly Thr Ala Lys Ser Val Thr Cys Thr Tyr
        115                 120                 125

Ser Pro Ala Leu Asn Lys Met Phe Cys Gln Leu Ala Lys Thr Cys Pro
130                 135                 140

Val Gln Leu Trp Val Asp Ser Thr Pro Pro Gly Thr Arg Val Arg
145                 150                 155                 160

Ala Met Ala Ile Tyr Lys Gln Ser Gln His Met Thr Glu Val Val Arg
                165                 170                 175

Arg Cys Pro His His Glu Arg Cys Ser Asp Ser Asp Gly Leu Ala Pro
            180                 185                 190

Pro Gln His Leu Ile Arg Val Glu Gly Asn Leu Arg Val Glu Tyr Leu
        195                 200                 205

Asp Asp Arg Asn Thr Phe Arg His Ser Val Val Val Pro Tyr Glu Pro
    210                 215                 220

Pro Glu Val Gly Ser Asp Cys Thr Thr Ile His Tyr Asn Tyr Met Cys
225                 230                 235                 240

Asn Ser Ser Cys Met Gly Gly Met Asn Arg Arg Pro Ile Leu Thr Ile
                245                 250                 255

Ile Thr Leu Glu Asp Ser Ser Gly Asn Leu Leu Gly Arg Asn Ser Phe
            260                 265                 270

Glu Val Arg Val Cys Ala Cys Pro Gly Arg Asp Arg Arg Thr Glu Glu
        275                 280                 285

Glu Asn Leu Arg Lys Lys Gly Glu Pro His His Glu Leu Pro Pro Gly
    290                 295                 300

Ser Thr Lys Arg Ala Leu Pro Asn Asn Thr Ser Ser Ser Pro Gln Pro
```

-continued

```
            305                 310                 315                 320
Lys Lys Lys Pro Leu Asp Gly Glu Tyr Phe Thr Leu Gln Ile Arg Gly
                    325                 330                 335

Arg Glu Arg Phe Glu Met Phe Arg Glu Leu Asn Glu Ala Leu Glu Leu
                340                 345                 350

Lys Asp Ala Gln Ala Gly Lys Glu Pro Gly Gly Ser Arg Ala His Ser
            355                 360                 365

Ser His Leu Lys Ser Lys Gly Ser Thr Ser Arg His Lys Lys Leu
        370                 375                 380

Met Arg Lys Thr Glu Gly Pro Asp Ser Asp
385                 390

<210> SEQ ID NO 5
<211> LENGTH: 50
<212> TYPE: PRT
<213> ORGANISM: Homo sapiens

<400> SEQUENCE: 5

Gly Met Leu Asn Asn His Gly His Ala Val Pro Ala Asn Gly Glu Met
1               5                   10                  15

Ser Ser Ser His Ser Ala Gln Ser Met Val Ser Gly Ser His Cys Thr
            20                  25                  30

Pro Pro Pro Pro Tyr His Ala Asp Pro Ser Leu Val Ser Phe Leu Thr
        35                  40                  45

Gly Leu
    50

<210> SEQ ID NO 6
<211> LENGTH: 49
<212> TYPE: PRT
<213> ORGANISM: Homo sapiens

<400> SEQUENCE: 6

Gly Met Leu Asn Asn His Gly His Ala Val Pro Ala Asn Gly Glu Met
1               5                   10                  15

Ser Ser Ser His Ser Ala Gln Ser Met Val Ser Gly Ser His Cys Thr
            20                  25                  30

Pro Pro Pro Pro Tyr His Ala Asp Pro Ser Leu Val Arg Thr Trp Gly
        35                  40                  45

Pro

<210> SEQ ID NO 7
<211> LENGTH: 218
<212> TYPE: PRT
<213> ORGANISM: Loligo forbesi

<400> SEQUENCE: 7

Gly Gly Met Asn Lys Leu Pro Ser Val Asn Gln Leu Val Gly Gln Pro
1               5                   10                  15

Pro Pro His Ser Ser Ala Ala Thr Pro Asn Leu Gly Pro Val Gly Pro
            20                  25                  30

Gly Met Leu Asn Asn His Gly His Ala Val Pro Ala Asn Gly Glu Met
        35                  40                  45

Ser Ser Ser His Ser Ala Gln Ser Met Val Ser Gly Ser His Cys Thr
    50                  55                  60

Pro Pro Pro Pro Tyr His Ala Asp Pro Ser Leu Val Ser Phe Leu Thr
65                  70                  75                  80
```

-continued

Gly Leu Gly Cys Pro Asn Cys Ile Glu Tyr Phe Thr Ser Gln Gly Leu
                85                  90                  95

Gln Ser Ile Tyr His Leu Gln Asn Leu Thr Ile Glu Asp Leu Gly Ala
            100                 105                 110

Leu Lys Ile Pro Glu Gln Tyr Arg Met Thr Ile Trp Arg Gly Leu Gln
        115                 120                 125

Asp Leu Lys Gln Gly His Asp Tyr Ser Thr Ala Gln Gln Leu Leu Arg
    130                 135                 140

Ser Ser Asn Ala Ala Thr Ile Ser Ile Gly Gly Ser Gly Glu Leu Gln
145                 150                 155                 160

Arg Gln Arg Val Met Glu Ala Val His Phe Arg Val Arg His Thr Ile
                165                 170                 175

Thr Ile Pro Asn Arg Gly Gly Pro Gly Gly Pro Asp Glu Trp Ala
            180                 185                 190

Asp Phe Gly Phe Asp Leu Pro Asp Cys Lys Ala Arg Lys Gln Pro Ile
        195                 200                 205

Lys Glu Glu Phe Thr Glu Ala Glu Ile His
    210                 215

<210> SEQ ID NO 8
<211> LENGTH: 20
<212> TYPE: PRT
<213> ORGANISM: Homo sapiens

<400> SEQUENCE: 8

Glu Pro Pro Leu Ser Gln Glu Thr Phe Ser Asp Leu Trp Lys Leu Leu
1               5                   10                  15

Pro Glu Asn Asn
            20

<210> SEQ ID NO 9
<211> LENGTH: 13
<212> TYPE: PRT
<213> ORGANISM: Chlorocebus sabaeus

<400> SEQUENCE: 9

Thr Phe Glu His Leu Trp Ser Ser Leu Glu Pro Asp Ser
1               5                   10

<210> SEQ ID NO 10
<211> LENGTH: 20
<212> TYPE: PRT
<213> ORGANISM: Chlorocebus sabaeus

<400> SEQUENCE: 10

Glu Pro Pro Leu Ser Gln Glu Thr Phe Ser Asp Leu Trp Lys Leu Leu
1               5                   10                  15

Pro Glu Asn Asn
            20

<210> SEQ ID NO 11
<211> LENGTH: 20
<212> TYPE: PRT
<213> ORGANISM: Macaca mulatta

<400> SEQUENCE: 11

Glu Pro Pro Leu Ser Gln Glu Thr Phe Ser Asp Leu Trp Lys Leu Leu
1               5                   10                  15

Pro Glu Asn Asn
            20

<210> SEQ ID NO 12
<211> LENGTH: 6
<212> TYPE: PRT
<213> ORGANISM: Canis lupis familiaris

<400> SEQUENCE: 12

Leu Leu Pro Glu Asn Asn
 1               5

<210> SEQ ID NO 13
<211> LENGTH: 19
<212> TYPE: PRT
<213> ORGANISM: Felis catus

<400> SEQUENCE: 13

Pro Pro Leu Ser Gln Glu Thr Phe Ser Glu Leu Trp Asn Leu Leu Pro
 1               5                  10                  15

Glu Asn Asn

<210> SEQ ID NO 14
<211> LENGTH: 20
<212> TYPE: PRT
<213> ORGANISM: Bos taurus

<400> SEQUENCE: 14

Glu Pro Pro Leu Ser Gln Glu Thr Phe Ser Asp Leu Trp Asn Leu Leu
 1               5                  10                  15

Pro Glu Asn Asn
            20

<210> SEQ ID NO 15
<211> LENGTH: 20
<212> TYPE: PRT
<213> ORGANISM: Ovis aries

<400> SEQUENCE: 15

Glu Pro Pro Leu Ser Gln Glu Thr Phe Ser Asp Leu Trp Asn Leu Leu
 1               5                  10                  15

Pro Glu Asn Asn
            20

<210> SEQ ID NO 16
<211> LENGTH: 20
<212> TYPE: PRT
<213> ORGANISM: Oryctolagus cuniculus

<400> SEQUENCE: 16

Glu Pro Pro Leu Ser Gln Glu Thr Phe Ser Asp Leu Trp Lys Leu Leu
 1               5                  10                  15

Pro Glu Asn Asn
            20

<210> SEQ ID NO 17
<211> LENGTH: 10
<212> TYPE: PRT
<213> ORGANISM: Spermophilus beecheyi

<400> SEQUENCE: 17

Asp Leu Trp Asn Leu Leu Pro Glu Asn Asn
 1               5                  10

```
<210> SEQ ID NO 18
<211> LENGTH: 20
<212> TYPE: PRT
<213> ORGANISM: Rattus norvegicus

<400> SEQUENCE: 18

Glu Leu Pro Leu Ser Gln Glu Thr Phe Ser Cys Leu Trp Lys Leu Leu
1               5                   10                  15

Pro Pro Asp Asp
            20

<210> SEQ ID NO 19
<211> LENGTH: 20
<212> TYPE: PRT
<213> ORGANISM: Cricetulus griseus

<400> SEQUENCE: 19

Glu Leu Pro Leu Ser Gln Glu Thr Phe Ser Asp Leu Trp Lys Leu Leu
1               5                   10                  15

Pro Pro Asn Asn
            20

<210> SEQ ID NO 20
<211> LENGTH: 20
<212> TYPE: PRT
<213> ORGANISM: Mus musculus

<400> SEQUENCE: 20

Glu Leu Pro Leu Ser Gln Glu Thr Phe Ser Gly Leu Trp Lys Leu Leu
1               5                   10                  15

Pro Pro Glu Asp
            20

<210> SEQ ID NO 21
<211> LENGTH: 11
<212> TYPE: PRT
<213> ORGANISM: Gallus gallus

<400> SEQUENCE: 21

Glu Val Phe Met Asp Leu Trp Ser Met Leu Pro
1               5                   10

<210> SEQ ID NO 22
<211> LENGTH: 18
<212> TYPE: PRT
<213> ORGANISM: Oncorhynchus mykiss

<400> SEQUENCE: 22

Ser Leu Pro Leu Ser Gln Glu Ser Phe Glu Asp Leu Trp Lys Met Asn
1               5                   10                  15

Leu Asn

<210> SEQ ID NO 23
<211> LENGTH: 16
<212> TYPE: PRT
<213> ORGANISM: Xenopus laevis

<400> SEQUENCE: 23

Pro Leu Ser Gln Glu Thr Phe Glu Asp Leu Trp Ser Leu Leu Pro Asp
1               5                   10                  15

<210> SEQ ID NO 24
<211> LENGTH: 15
```

```
<212> TYPE: PRT
<213> ORGANISM: Loligo forbesi

<400> SEQUENCE: 24

Ser Gln Glu Thr Phe Asn Leu Leu Trp Asp Ser Leu Glu Ala Asn
 1               5                  10                  15

<210> SEQ ID NO 25
<211> LENGTH: 4
<212> TYPE: PRT
<213> ORGANISM: Dictyostelium discoideum

<400> SEQUENCE: 25

Leu Ser Lys Leu
 1

<210> SEQ ID NO 26
<211> LENGTH: 33
<212> TYPE: DNA
<213> ORGANISM: Artificial
<220> FEATURE:
<223> OTHER INFORMATION: Synthetic Oligonucleotide

<400> SEQUENCE: 26

CGCGGATCCT TGGTGCCGCA GCCGCTGGTA GAC                           33

<210> SEQ ID NO 27
<211> LENGTH: 33
<212> TYPE: DNA
<213> ORGANISM: Artificial
<220> FEATURE:
<223> OTHER INFORMATION: Synthetic Oligonucleotide

<400> SEQUENCE: 27

TAGCCAATTG TCAGTGGATC TCGGCTCCGT GAA                           33
```